(12) United States Patent
Py

(10) Patent No.: US 10,265,480 B2
(45) Date of Patent: Apr. 23, 2019

(54) MULTIPLE DOSE DEVICE AND METHOD

(71) Applicant: Dr. Py Institute LLC, New Milford, CT (US)

(72) Inventor: Daniel Py, Larchmont, NY (US)

(73) Assignee: DR. PY INSTITUTE LLC, New Milford, CT (US)

( * ) Notice: Subject to any disclaimer, the term of this patent is extended or adjusted under 35 U.S.C. 154(b) by 380 days.

(21) Appl. No.: 14/963,170

(22) Filed: Dec. 8, 2015

(65) Prior Publication Data

US 2016/0089502 A1 Mar. 31, 2016

Related U.S. Application Data

(62) Division of application No. 13/743,661, filed on Jan. 17, 2013, now Pat. No. 9,205,198.

(Continued)

(51) Int. Cl.
*A61M 5/315* (2006.01)
*B05B 11/00* (2006.01)

(Continued)

(52) U.S. Cl.
CPC ....... *A61M 5/31593* (2013.01); *B05B 11/007* (2013.01); *B05B 11/0072* (2013.01);

(Continued)

(58) Field of Classification Search
CPC .............. A61M 5/31593; A61M 5/204; A61M 2005/3126; A61M 2005/3128;

(Continued)

(56) References Cited

U.S. PATENT DOCUMENTS 4,301,948 A 11/1981 Czech et al.
5,456,672 A 10/1995 Diederich et al.
(Continued)

FOREIGN PATENT DOCUMENTS

WO 2011073916 A1 6/2011

OTHER PUBLICATIONS

International Search Report and Written Opinion dated May 6, 2013 for International Application No. PCT/US2013/021865. 14 pages.

*Primary Examiner* — Amber R Stiles
(74) *Attorney, Agent, or Firm* — McCarter & English, LLP

(57) ABSTRACT

A multiple dose syringe has a first valve defining a first valve opening pressure and a second valve defining a second valve opening pressure. A storage chamber in fluid communication with the second valve stores multiple doses of a substance therein and includes an outlet for dispensing multiple doses of the stored substance therethrough. A compression surface is movable between first and second positions and defines a compression chamber between the compression surface and the first valve. Movement of the compression surface in a direction from the first position toward the second position dispenses substance in the compression chamber through the first valve and out of the syringe. Movement of the compression surface in a direction from the second position toward the first position causes substance to flow from the storage chamber through the second valve and into the compression chamber.

32 Claims, 21 Drawing Sheets

Related U.S. Application Data

(60) Provisional application No. 61/587,500, filed on Jan. 17, 2012.

(51) Int. Cl.

| | | |
|---|---|---|
| *B65D 83/14* | (2006.01) | |
| *G01F 11/02* | (2006.01) | |
| *A61M 5/178* | (2006.01) | |
| *A61J 7/00* | (2006.01) | |
| *A61M 5/31* | (2006.01) | |
| *A61M 5/20* | (2006.01) | |
| *B05B 9/04* | (2006.01) | |

(52) U.S. Cl.
CPC .... *B05B 11/00416* (2018.08); *B05B 11/3015* (2013.01); *B05B 11/3028* (2013.01); *B05B 11/3064* (2013.01); *B05B 11/3077* (2013.01); *B65D 83/7535* (2013.01); *G01F 11/02* (2013.01); *G01F 11/025* (2013.01); *G01F 11/027* (2013.01); *A61J 7/0053* (2013.01); *A61M 5/1782* (2013.01); *A61M 5/204* (2013.01); *A61M 2005/3126* (2013.01); *A61M 2005/3128* (2013.01); *B05B 9/0426* (2013.01); *G01F 11/028* (2013.01)

(58) Field of Classification Search
CPC .. A61M 5/1782; G01F 11/027; G01F 11/025; G01F 11/02; G01F 11/028; B05B 11/3064; B05B 11/3015; B05B 11/0048; B05B 11/0072; B05B 11/3077; B05B 11/007; B05B 11/3028; B05B 9/0426; B65D 83/7535; A61J 7/0053
See application file for complete search history.

(56) References Cited

U.S. PATENT DOCUMENTS

| | | | |
|---|---|---|---|
| 5,591,136 A * | 1/1997 | Gabriel | A61M 5/31553 604/208 |
| 5,687,884 A | 11/1997 | Bodin et al. | |
| 5,843,042 A * | 12/1998 | Ren | A61J 1/20 604/207 |
| 6,364,861 B1 | 4/2002 | Feith et al. | |
| 6,475,193 B1 * | 11/2002 | Park | A61M 5/204 604/191 |
| 6,942,643 B2 | 9/2005 | Eakins et al. | |
| 2001/0009994 A1 * | 7/2001 | Small | A61J 3/002 604/513 |
| 2001/0044603 A1 | 11/2001 | Harrold | |
| 2005/0090805 A1 * | 4/2005 | Shaw | A61M 39/26 604/523 |
| 2005/0165368 A1 | 7/2005 | Py et al. | |
| 2005/0197538 A1 | 9/2005 | Leaton et al. | |
| 2008/0118299 A1 | 5/2008 | Py et al. | |
| 2008/0135586 A1 * | 6/2008 | Pardes | B65D 47/205 222/494 |
| 2009/0247961 A1 * | 10/2009 | Carlyon | A61M 5/28 604/237 |
| 2010/0187260 A1 | 7/2010 | Stadelhofer et al. | |
| 2010/0256574 A1 | 10/2010 | Simpson et al. | |
| 2010/0268168 A1 | 10/2010 | Cole et al. | |

\* cited by examiner

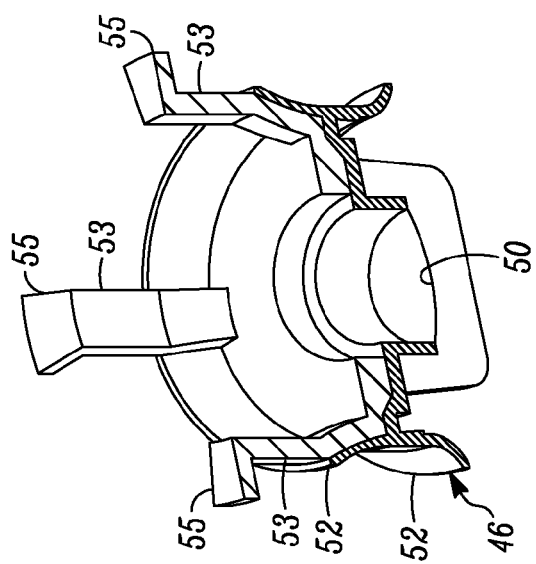
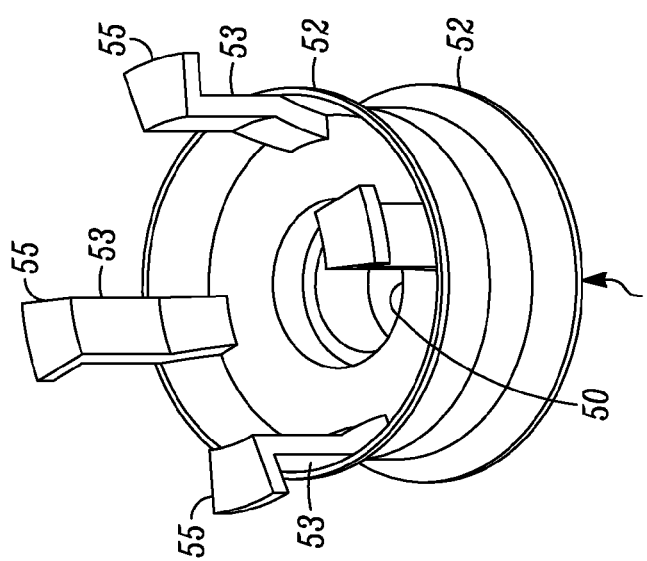

MULTIPLE DOSE DEVICE AND METHOD

CROSS-REFERENCE TO RELATED APPLICATION

This patent application is a divisional of U.S. patent application Ser. No. 13/743,661 filed on Jan. 17, 2013, entitled "Multiple Dose Syringe and Method," which claims priority to U.S. Provisional Patent Application No. 61/587,500, filed Jan. 17, 2012, entitled "Multiple Dose Syringe and Method," which are hereby incorporated by reference in their entirety as part of the present disclosure.

FIELD OF THE INVENTION

The present invention relates to devices for dispensing substances, such as syringes, and more particularly, to such devices that can store multiple doses of the substances to be dispensed.

BACKGROUND INFORMATION

A typical syringe includes a body defining a cylindrical or barrel shape, a manually-engageable plunger slidably received within the body, an outlet for dispensing fluid pushed or compressed by the plunger therethrough, and a luer type fitting at the outlet of the body. A luer type fitting, such as sold under the trademark LUER-LOK®, is connectable to another luer fitting on a needle, for example, to form a luer connection between the needle and body. Typically, the needle defines a female luer fitting and the syringe body defines a male luer fitting that is receivable within the female luer fitting to form a leak-free connection between the needle and syringe body.

The luer taper is a standardized system of small-scale fluid fittings used for making leak-free connections between a male-taper fitting and its mating female part on medical and laboratory instruments, including hypodermic syringe tips, needles and stopcocks. Luer_locking fittings are securely joined by means of a tabbed hub on the female fitting which screws into threads in a sleeve on the male fitting. Luer-slip fittings conform to luer taper dimensions and are pressed together and held by friction without any threads. Luer components are manufactured either from metal or plastic and are available from many companies worldwide.

One of the drawbacks of known syringes is that they are not as effective as desired for dispensing multiple doses of substances, such as medicaments, pharmaceuticals, vaccines, liquid nutrition products, supplements, or other products. A typical prior art syringe is prefilled with a unit dose, and therefore it can be used once on a single patient. Other syringes that are not prefilled have significant drawbacks if used to dispense multiple doses. Dosage metering can be inaccurate and difficult to control. The substance in the body of the syringe to be dispensed is in open fluid communication through the outlet port with the luer connection and/or the needle connected thereto. Any germs, bacteria, or other contaminants at the needle or luer connection, for example, can travel into the body of the syringe and contaminate the remaining substance stored therein. Thus, although a luer connection allows a needle to be discarded after single patient use and replaced with a fresh needle, the substance in the syringe body nevertheless can become contaminated during or between dispensing multiple doses. This, in turn, can lead to the spread of germs, bacteria or other contaminants from one patient to another and give rise to harmful results.

SUMMARY OF THE INVENTION

It is an object of the present invention to overcome one or more of the above-described drawbacks and/or disadvantages of the prior art.

In accordance with a first aspect, a multiple dose device, such as a syringe, comprises a first valve defining a first valve opening pressure. A storage chamber stores multiple doses of a substance therein and includes a storage chamber outlet for dispensing multiple doses of the stored substance therethrough. A second valve is in fluid communication with the storage chamber outlet and defines a second valve opening pressure. A compression surface is movable between first and second positions and the compression chamber is defined between the compression surface and the first valve. Movement of the compression surface in a direction from the first position toward the second position creates a pressure differential across the first valve exceeding the first valve opening pressure and dispenses the dose of substance in the compression chamber through the first valve and out of the syringe. Movement of the compression surface in a direction from the second position toward the first position creates a pressure differential across the second valve exceeding the second valve opening pressure, and causes another dose of substance to flow from the storage chamber through the second valve and into the compression chamber.

In some embodiments, the compression surface and the first valve are located at opposing ends of the compression chamber.

In some embodiments, the syringe further comprises an actuator coupled to the compression surface for moving the compression surface between the first and second positions. A spring is coupled to the compression surface for moving, biasing, or at least assisting in movement of the compression surface between the first and second positions and/or between second and first positions. That is, the actuator moves the compression surface in the direction from the first position toward the second position, and the spring moves or biases the compression surface in the direction from the second position toward the first position. The actuator can be manually engageable.

In some embodiments, movement of the compression surface in the direction from the first position toward the second position pressurizes the substance in the compression chamber to a pressure exceeding the first valve opening pressure and dispenses the dose of substance in the compression chamber through the first valve. In some embodiments, movement of the compression surface in a direction from the second position toward the first position creates at least a partial vacuum in the compression chamber which, in turn, causes another dose of substance to flow from the storage chamber through the second valve and into the compression chamber.

In some embodiments, the first valve and/or second valve includes an elastic valve member defining a normally closed valve seam that substantially prevents the passage of fluid therethrough when a pressure differential across the valve is less than the respective valve opening pressure, and allows the passage of fluid therethrough when a pressure differential across the valve exceeds the respective valve opening pressure. In some such embodiments, the first and/or second valves include a relatively rigid valve seat, and the elastic valve member engages the valve seat and forms the valve seam therebetween. In some such embodiments (i) the elastic valve member defines a progressively decreasing wall thickness in a direction from an inlet toward an outlet of the valve seam, and/or (ii) the valve seat defines a progressively increasing width or diameter in a direction from an inlet toward an outlet of the valve seam.

In some embodiments, at least one of the first and second valves moves relative toward the other when the compression surface is moved from the first position toward the second position, and moves relative away from the other when the compression surface is moved from the second position toward the first position.

In some embodiments, at least one of the storage chamber and the first valve moves relative toward the other when the compression surface is moved from the first position toward the second position, and moves relative away from the other when the compression surface is moved from the second position toward the first position.

Some embodiments further comprise a body, wherein the first valve is located at a distal end of the body, the second valve and the compression chamber are located within the body, and the storage chamber is one of (i) located external to the body and (ii) located internal to the body.

Some embodiments further comprise a body and a plunger slidably received within the body. The first valve is located adjacent to a distal end of the body and the compression surface is located adjacent to a distal end of the plunger. In some such embodiments, the compression chamber is defined between the first valve and the second valve. In some such embodiments, the volume of the compression chamber in the first position corresponds approximately to the volume of a respective dose of substance to be dispensed through the first valve. Some embodiments further include a first seal between the plunger and the body. The first seal and the first valve seal the compression chamber with respect to ambient atmosphere. In some such embodiments, the first seal extends annularly about the plunger and allows sliding movement of the plunger and/or the body relative to the other between the first and second positions. Some syringes further comprise a second seal between the plunger and the body and spaced proximally relative to the first seal. The second seal seals the first seal and the portions of the plunger and/or the body contacted by the first seal with respect to ambient atmosphere.

In some embodiments, the storage chamber is located within the plunger. In some such embodiments, the storage chamber is a variable-volume storage chamber, the plunger includes a sliding seal axially spaced relative to the second valve, and the variable-volume storage chamber is defined between the sliding seal and the second valve. In some embodiments, the sliding seal includes a penetrable and resealable portion or septum that is penetrable by a needle or filling or injection member for filling the storage chamber with multiple doses of the substance to be dispensed, and is resealable to hermetically seal a resulting penetration aperture in the septum. The septum can be resealed by a liquid sealant, radiation, and/or the application of thermal energy thereto. In some embodiments, movement of the plunger in the direction from the second position toward the first position creates a pressure differential across the second valve exceeding the second valve opening pressure, causes another dose of substance to flow from the storage chamber through the second valve and into the compression chamber, and causes the sliding seal to move distally within the plunger to correspondingly reduce the volume of the storage chamber.

Some embodiments further comprise a spring normally biasing the plunger in the direction from the second position toward the first position. In some such embodiments, the plunger is manually depressible within the body in the direction from the first position toward the second position to dispense a dose of substance from the compression chamber through the first valve and out of the syringe. The spring biases the plunger to return from the second position to the first position and release another dose of substance from the variable-volume storage chamber into the compression chamber. In some embodiments, the plunger includes a first manually-engageable surface adjacent to a proximal end thereof that is manually engageable to depress the plunger in the direction from the first position toward the second position. The body includes a second manually-engageable surface projecting radially therefrom to allow a user to grip the body with the same hand used to manually depress the plunger. In some such embodiments, the plunger and/or the body includes a stop member and the other of the plunger and/or the body includes a stop surface. The stop member engages the stop surface in the first position to prevent further proximal movement of the plunger and/or body relative to the other.

Some embodiments further comprise a connector located at a distal end of the syringe downstream of the first valve and adapted to connect an administering member thereto for administering the dispensed dose of substance to a patient. The connector is adapted to connect thereto an administering member that is at least one of (i) a needle for injecting a dose of substance into a patient, and/or (ii) a shield to facilitate at least one of oral and nasal dosing of the substance to be dispensed. In some embodiments, the connector is a luer connector.

Some embodiments further comprise an elastic spring coupled between the plunger and body that normally biases the plunger in the direction from the second position toward the first position. In some such embodiments, the elastic spring is defined by a bellows. In other such embodiments, the elastic spring is approximately dome shaped. In some such embodiments, the spring defines the compression chamber.

In some embodiments, the storage chamber is located external to the body. Some such embodiments further include a pouch defining the storage chamber, and one or more conduits extending between an outlet of the pouch and an inlet of the second valve. Some such embodiments further comprise a sterile connector between an outlet of the storage chamber and the inlet of the second valve. The sterile connectors allow (i) plural storage chambers to be connected to a respective multiple dose syringe, and/or (ii) plural multiple dose syringes to be connected to a respective storage chamber.

In accordance with another aspect, a multiple dose device, such as a syringe, comprises first means for controlling the flow of fluid through an outlet of the syringe at a first opening pressure; second means for storing multiple doses of a substance therein sealed with respect to ambient atmosphere; third means in fluid communication with the second means for controlling the flow of substance through an outlet of the second means and at a second opening pressure; and fourth means for moving (i) in a direction from a first position toward a second position, for creating a pressure differential across the first means exceeding the first opening pressure, and for dispensing a dose of substance through the first means and out of the syringe or other device, and (ii) in a direction from the second position toward the first position, for creating a pressure differential across the third means exceeding the second opening pressure, and for causing another dose of substance to flow out of the second means and be ready for dispensing through the first means.

In some embodiments, the device further comprises sixth means for connecting an administering member therefor for administering the dispensed dose of substance to a patient. In some such embodiments, the device further comprises sixth means for moving the fourth means between the first and second positions.

In some embodiments, the first means is a first valve, the second means is a storage chamber, the third means is a second valve, the fourth means is a compression surface movable between the first and second positions, the fifth means is a connector, and the sixth means is a manually engageable actuator coupled to the compression surface.

In accordance with another aspect, a method comprises the following steps:
  i. storing multiple doses of a substance to be dispensed in a storage chamber of a syringe or other device;
  ii. releasing a dose of substance from the variable-volume storage chamber into a compression chamber of the syringe or other device;
  iii. compressing the dose of substance in the compression chamber above a first valve opening pressure of an outlet valve of the syringe or other device;
  iv. releasing the dose of substance through the outlet valve;
  v. maintaining the substance in the storage chamber and the compression chamber at least one of sterile and aseptic throughout steps i through iv; and
  vi. repeating steps ii through v with the same syringe or other device.

In some embodiments the compressing steps includes manually actuating an actuator to compress the dose of substance in the compression chamber above the valve opening pressure. Some embodiments further comprise moving a compression surface away from the outlet valve and, in turn, creating at least a partial vacuum in the compression chamber and causing another dose of substance to flow from the storage chamber into the compression chamber.

In some embodiments, the moving step includes biasing the compression surface in a direction away from the outlet valve and releasing the actuator.

In some embodiments, the creating step further comprises creating a pressure differential across a second valve located between the variable volume storage chamber and the compression chamber exceeding a second valve opening pressure thereof, and, the causing step includes flowing the another dose through the second valve.

In some embodiments, the second valve comprises an inlet valve of the syringe.

Some embodiments further comprise maintaining the substance in a variable-volume storage chamber hermetically sealed with respect to ambient atmosphere throughout steps i through iv.

Some embodiments further include parenterally or enterally administering the released dose of substance to the patient. In some such embodiments, the administering step includes (i) injecting the dose of substance through a needle coupled in fluid communication with the outlet valve, or (ii) orally or nasally administering the dose of substance to the patient. Some such embodiments further comprise connecting a disposable shield adjacent to the outlet valve to facilitate oral or nasal administration of the dose of substance to the patient.

Some embodiments further include fluidically connecting the storage chamber to the compression chamber through a sterile connector. Some such embodiments include preventing the sterile connector from being disconnected after connecting the storage chamber and compression chamber and thereby preventing more than one storage chamber from being connected to the respective syringe.

One advantage of the present invention is that the syringe or other device can effectively dispense multiple doses of a substance, such as medicaments, pharmaceuticals, vaccines, liquid nutrition products, supplements, and any of numerous other products that are currently known, or that later become known. Another advantage is that the substance to be dispensed is sealed within the storage chamber until it is dispensed, and therefore the substance can be maintained sterile, aseptic and/or contamination free within the storage chamber throughout the dispensing of multiple doses to different patients. The outlet valve prevents germs, bacteria or other contaminants at, for example, the needle or luer connection, from traveling into the body of the syringe or storage chamber.

Other objects and advantages of the present invention, and/or of the currently preferred embodiments thereof, will become more readily apparent in view of the following detailed description of embodiments and accompanying drawings.

BRIEF DESCRIPTION OF THE DRAWINGS

FIG. 6A is a perspective top view of the sliding seal of the syringe of FIGS. 1 through 5.

FIG. 6B is a perspective cross-sectional view of the sliding seal of the syringe of FIGS. 1 through 5.

DETAILED DESCRIPTION OF EMBODIMENTS OF THE INVENTION

Figure 1:
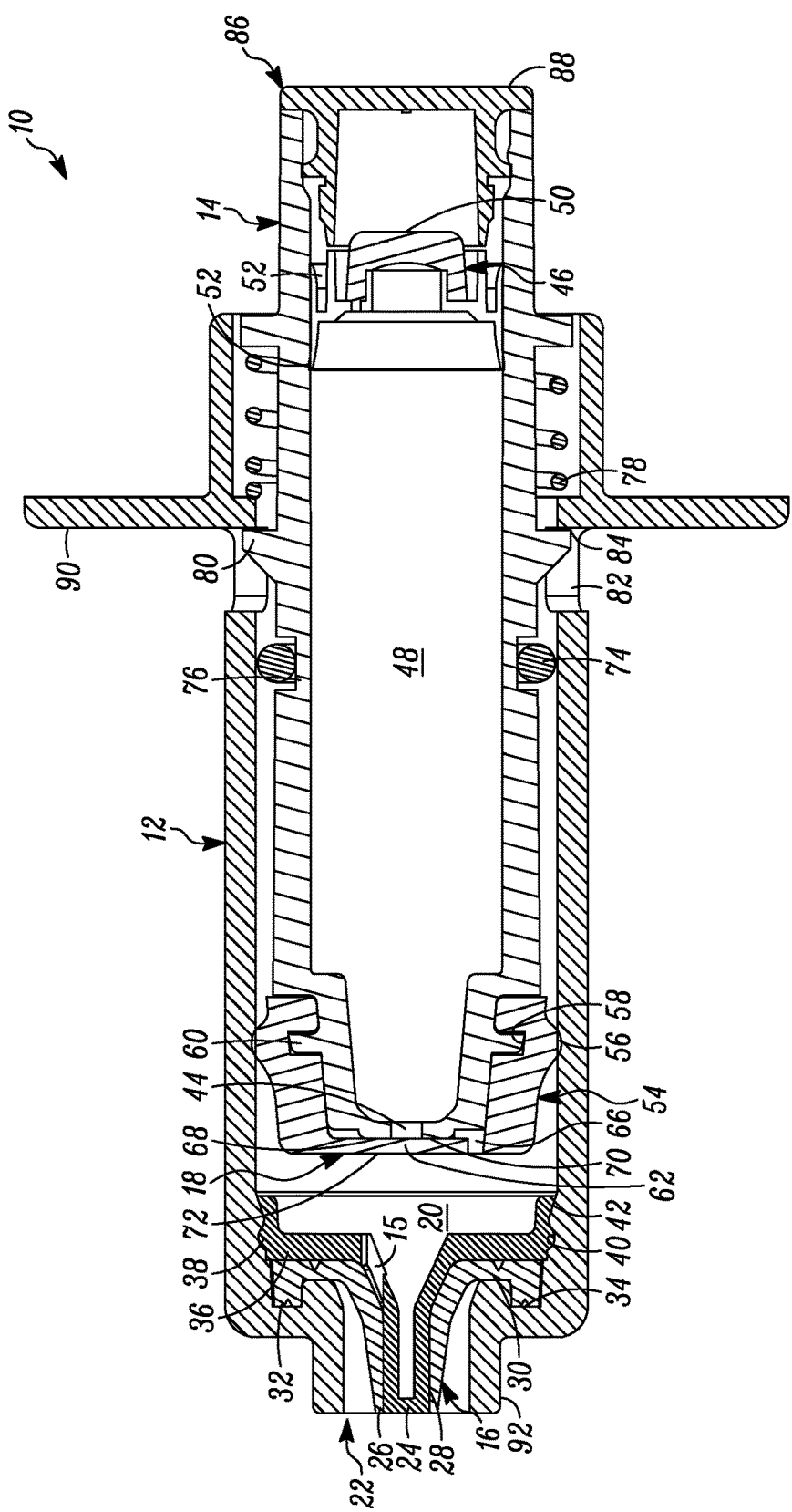
FIG. 1 is a cross-sectional view of a first embodiment of a syringe including a variable-volume storage chamber within the plunger of the syringe and showing the plunger in the first or unactuated position.

In FIG. 1 a device is indicated generally by the reference numeral 10. In the illustrated embodiment, the device 10 is a multiple dose syringe; however, as may be recognized by those skilled in the pertinent art based on the teachings herein, the invention may be embodied in and otherwise may be applicable to devices other than multiple dose syringes. The device or syringe 10 includes a body 12, an actuator or plunger 14, a first one-way valve 16 located adjacent to a distal end of the body 12, a second one-way valve 18 located adjacent to a distal end of the plunger 14, and a compression chamber 20 coupled in fluid communication between an inlet 15 of the first valve 16 and an outlet of the second valve 18.

The first valve 16 is coupled to the body 12 at the distal end thereof. The first valve 16 is in fluid communication with the compression chamber 20 at a proximal side thereof and is in fluid communication with an outlet 22 of the syringe 10 at a distal side thereof. The first valve 16 includes a relatively rigid first valve seat 24 and a surrounding flexible first valve member or cover 26 mounted over the first valve seat 24 and defining an axially-elongated, annular first valve seam 28 therebetween. The first valve member 26 in some embodiments forms an interference fit with the first valve seat 24 to thereby form a fluid-tight seal in a normally closed position and, in turn, maintain the substance within the compression chamber 20 in a sterile and hermetically sealed condition. The constructions and/or configuration of the first valve 16 defines a first valve opening pressure, and remains in a normally closed position unless a pressure differential across the first valve 16 exceeds the first valve opening pressure. As shown in FIGS. 1-4, the first valve member 26 defines a substantially tapered cross-sectional shape moving in the axial direction from an inlet towards an outlet of the first valve seam 28. This configuration requires progressively less energy to open each respective annular portion of the valve when moving axially from the interior toward the exterior of the valve 16. Alternatively, or in combination with the tapered first valve member 26, the first valve seat 24 may define an outer diameter that progressively or otherwise increases in the axial direction from the inlet towards the outlet of the first valve seam 28, to provide the same or similar effect. As a result, once the valve is opened at the inlet 15, the pressure is sufficient to cause the downstream segments or portions of the first valve member 26 to progressively open and then close after passage of substance through the respective portion of the first valve seam 28 when moving in the direction from the inlet towards the outlet of the first valve seam 28 to dispense a dosage of substance. Also, in some embodiments, at any time when dispensing a dosage of substance, at least one of the plurality of segments of the first valve member 26 engages the first valve seat 24 to maintain a fluid-tight seal across the first valve 16, and thereby prevent an ingress of germs, bacteria or other unwanted substances through the first valve and into the body 12.

The first valve member 26 includes a base 30 defining an axially-extending annular protuberance 32 received within a corresponding annular recess 34 formed at the interior, distal end of the syringe body 12 adjacent to the syringe outlet 22 to fixedly secure the first valve member 26 in place. In the illustrated embodiment, the first valve member 26 is overmolded or otherwise co-molded to the syringe body 12 with the base 30 and the annular protuberance 32 fixedly secured to the corresponding surfaces of the syringe body, as shown. The first valve seat 24 includes a base 36 defining a laterally-extending annular protuberance 38 received within a corresponding annular recess 40 formed in a side wall of the syringe body 12 proximally adjacent to the annular recess 34. As shown in FIGS. 1-4, the first valve seat 24 is received within the first valve member 26, and when the first valve seat protuberance 38 is received within the corresponding annular recess 40 of the syringe body 12, the valve seat base 36 engages the valve member base 30 to thereby form a fluid tight seal between the first valve 16 and the syringe body 12 (and thus between the compression chamber 20 and ambient atmosphere). As also shown in FIGS. 1-4, the syringe body 12 defines a tapered protuberance 42 formed proximally adjacent to the annular recess 40. As can be seen, the tapered protuberance 42 defines a tapered surface on the proximal side thereof to allow the first valve seat base 36 to slide over the protuberance when assembling the first valve seat 24 within the first valve member 26, but to prevent removal of the first valve seat 24 from the syringe body 12 once snap fit or otherwise received within the annular recess 40 of the syringe body 12.

Figure 3:
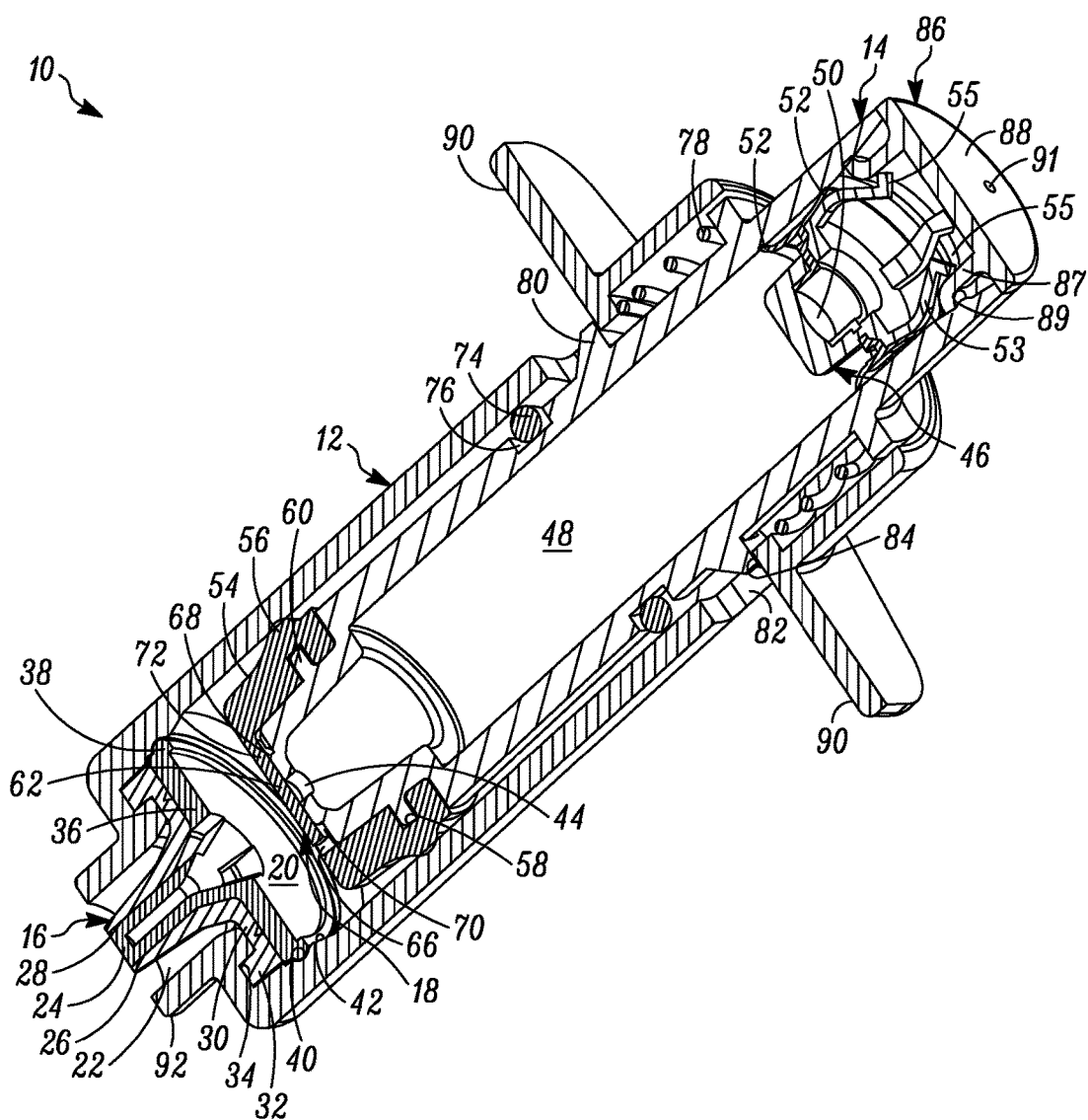
FIG. 3 is a second perspective cross-sectional view of the syringe of FIG. 1.
Figure 4:
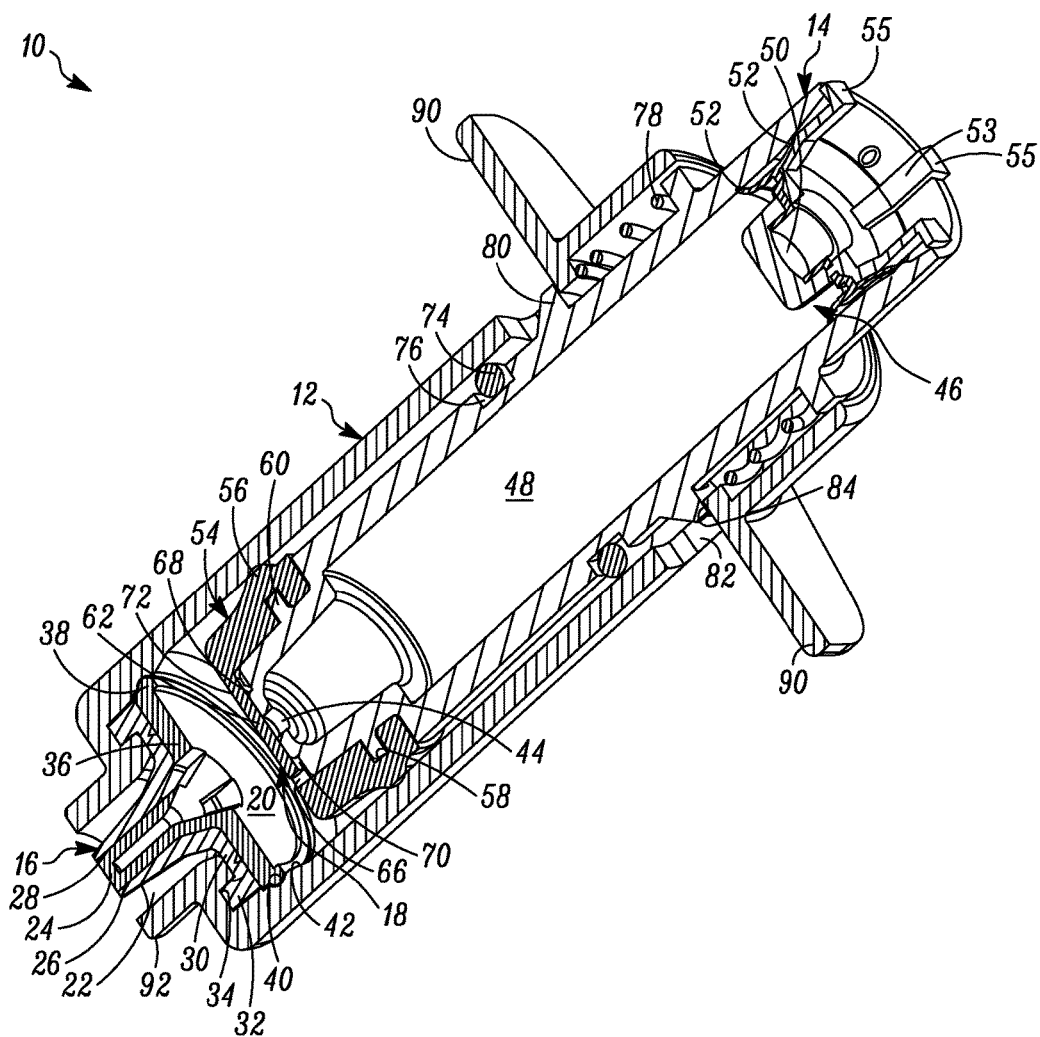
FIG. 4 is the same view as FIG. 3, but with the cap on the proximal end of the plunger removed.

The plunger 14 includes a storage chamber outlet 44 engaging the second valve 18 at the distal end of the plunger. A sliding seal 46 is received within an opposite end of the plunger 14 relative to the storage chamber outlet 44, and a variable-volume storage chamber 48 is defined within the hollow body of the plunger between the sliding seal 46 and outlet 44 for storing therein multiple doses of a substance to be dispensed. As best shown in FIG. 6B, the sliding seal 46 includes a penetrable and resealable septum 50 that is penetrable by a needle, filling or injection member (not shown) for sterile or aseptically filling the storage chamber 48 with multiple doses of the substance to be stored therein. The septum 50, in some embodiments, is formed of a material that is sufficiently elastic to close itself after withdrawal of the needle or other filling or injection member therefrom to thereby ensure that the head loss left by a residual penetration hole after the injection member is withdrawn prevents fluid ingress therethrough. Although the septum 50 is self-closing, the septum may be resealed by liquid sealant such as silicone or a silicone-based sealant, and/or the application of radiation or energy thereto to hermetically seal the substance within the storage chamber 48 from the ambient atmosphere and thereby maintain the sterility of the substance. The sliding seal 46 further includes at least one, and in the embodiment shown, two, axially spaced outer annular sealing members or portions 52 that sealingly engage a side wall of the plunger to form a fluid-tight seal therebetween. The sealing members or portions 52 may be formed integral with the sliding seal, such as by forming thereon annular protuberances, as shown, or may be formed by sealing members, such as o-rings or other sealing members, that are received within corresponding grooves or recesses formed in the sliding seal. As best shown in FIGS. 6A and 6B, the sliding seal 46 includes a plurality of angularly spaced, axially extending legs 53. As shown in FIG. 4, the tabbed ends 55 of the legs 53 are engageable with a proximal edge of the plunger 14 to fixedly secure the axial position of the sliding seal 46 during sterile filling of the variable-volume storage chamber 48 therethrough. As shown in FIG. 3, after the variable-volume storage chamber 48 is filled through the needle penetrable septum 50 and the needle or like filling or injection member is withdrawn, the tabbed ends 55 of the legs 53 are disengaged from the proximal end of the plunger 14 to allow the sliding seal 46 to move axially within the plunger, as described further below.

The sliding seal 46, the manner in which it cooperates with the plunger to define the variable-volume storage chamber 48, and the manner in which it is penetrated and resealed in order to sterile fill the variable-volume storage chamber, may be the same as or substantially similar to that disclosed in any of the following patents and patent applications, each of which is hereby expressly incorporated by reference in its entirety as part of the present disclosure: U.S. patent application Ser. No. 13/219,597, filed Aug. 26, 2011, entitled "Laterally-Actuated Dispenser with One-Way Valve For Storing and Dispensing Substances," which is a continuation of U.S. patent application Ser. No. 12/710,516, filed Feb. 23, 2010, entitled "Laterally-Actuated Dispenser with One-Way Valve for Storing and Dispensing Metered Amounts of Substances," now U.S. Pat. No. 8,007,193, which is a continuation of similarly titled U.S. patent application Ser. No. 11/237,599, filed Sep. 27, 2005, now U.S. Pat. No. 7,665,923, which, in turn, claims the benefit of similarly titled U.S. Provisional Patent Application No. 60/613,583, filed Sep. 27, 2004, and similarly titled U.S. Provisional Application No. 60/699,607 filed Jul. 15, 2005; and U.S. Patent Application entitled "Multiple Dose Vial and Method," filed on even date herewith, which, in turn, claims the benefit of similarly titled U.S. Provisional Patent Application No. 61/587,525, filed Jan. 17, 2012.

The septum 50 may be penetrated for sterile filling the variable-volume storage chamber 48 and resealed, such as by the application of radiation or energy thereto, e.g., laser radiation or energy, to hermetically seal the filled substance within the storage chamber, in accordance with the teachings of any of the following patents and patent applications, each of which is hereby expressly incorporated by reference in its entirety as part of the present disclosure: U.S. patent application Ser. No. 12/254,789, filed Oct. 20, 2008, entitled "Container Having a Closure and Removable Resealable Stopper for Sealing a Substance Therein and Related Method," which, in turn, claims the benefit of U.S. Patent Application No. 60/981,107, filed Oct. 18, 2007, entitled "Container Having a Closure and Removable Resealable Stopper for Sealing a Substance Therein;" U.S. patent application Ser. No. 12/245,678, filed Oct. 3, 2008, entitled "Apparatus For Formulating and Aseptically Filling Liquid Products," and U.S. patent application Ser. No. 12/245,681, filed Oct. 3, 2008, entitled "Method For Formulating and Aseptically Filling Liquid Products," which, in turn, claim the benefit of U.S. Patent Application No. 60/997,675, filed Oct. 4, 2007, entitled "Apparatus and Method for Formulating and Aseptically Filling Liquid Products;" U.S. patent application Ser. No. 12/875,440, filed Sep. 3, 2010, entitled "Device with Needle Penetrable and Laser Resealable Portion and Related Method," now U.S. Pat. No. 7,980,276, which is a divisional of U.S. patent application Ser. No. 12/371,386, filed Feb. 13, 2009, entitled "Device with Needle Penetrable and Laser Resealable Portion," now U.S. Pat. No. 7,810,529, which is a continuation of U.S. patent application Ser. No. 11/949,087, filed Dec. 3, 2007, entitled "Device with Needle Penetrable and Laser Resealable Portion and Related Method," now U.S. Pat. No. 7,490,639, which is a continuation of similarly titled U.S. patent application Ser. No. 11/879,485, filed Jul. 16, 2007, now U.S. Pat. No. 7,445,033, which is a continuation of similarly titled U.S. patent application Ser. No. 11/408,704, filed Apr. 21, 2006, now U.S. Pat. No. 7,243,689, which is a continuation of U.S. patent application Ser. No. 10/766,172, filed Jan. 28, 2004, entitled "Medicament Vial Having a Heat-Sealable Cap, and Apparatus and Method for Filling the Vial," now U.S. Pat. No. 7,032,631, which is a continuation-in-part of similarly titled U.S. patent application Ser. No. 10/694,364, filed Oct. 27, 2003, now U.S. Pat. No. 6,805,170 which is a continuation of similarly titled U.S. patent application Ser. No. 10/393,966, filed Mar. 21, 2003, now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application No. 60/182,139, filed Feb. 11, 2000, and similarly titled U.S. Provisional Patent Application No. 60/443,526, filed Jan. 28, 2003, and similarly titled U.S. Provisional Patent Application No. 60/484,204, filed Jun. 30, 2003; U.S. patent application Ser. No. 13/193,662, filed Jul. 29, 2011, entitled "Sealed Contained and Method of Filling and Resealing Same," which is a continuation of U.S. patent application Ser. No. 12/791,629, filed Jun. 1, 2010, entitled "Sealed Containers and Methods of Making and Filling Same," now U.S. Pat. No. 7,992,597, which is a divisional of U.S. patent application Ser. No. 11/515,162, filed Sep. 1, 2006, entitled "Sealed Containers and Methods of Making and Filling Same," now U.S. Pat. No. 7,726,352, which is a continuation of U.S. patent application Ser. No. 10/655,455, filed Sep. 3, 2003, entitled "Sealed Containers and Methods of Making and Filling Same," now U.S. Pat. No. 7,100,646, which is a continuation-in-part of U.S. patent application Ser. No. 10/393,966, filed Mar. 21, 2003, entitled "Medicament Vial Having A Heat-Sealable Cap, and Apparatus and Method For Filling The Vial," now U.S. Pat. No. 6,684,916, which is a divisional of similarly titled U.S. patent application Ser. No. 09/781,846, filed Feb. 12, 2001, now U.S. Pat. No. 6,604,561, which, in turn, claims the benefit of similarly titled U.S. Provisional Patent Application No. 60/182,139, filed on Feb. 11, 2000, and U.S. Provisional Patent Application No. 60/408,068, filed Sep. 3, 2002, entitled "Sealed Containers and Methods Of Making and Filling Same;" U.S. patent application Ser. No. 12/627,655, filed Nov. 30, 2009, entitled "Adjustable Needle Filling and Laser Sealing Apparatus and Method," now U.S. Pat. No. 8,096,333, which is a continuation of similarly titled U.S. patent application Ser.

No. 10/983,178, filed Nov. 5, 2004, now U.S. Pat. No. 7,628,184, which, in turn, claims the benefit of U.S. Provisional Patent Application No. 60/518,267, filed Nov. 7, 2003, entitled "Needle Filling and Laser Sealing Station," and similarly titled U.S. Provisional Patent Application No. 60/518,685, filed Nov. 10, 2003; U.S. patent application Ser. No. 11/901,467, filed Sep. 17, 2007 entitled "Apparatus and Method for Needle Filling and Laser Resealing," which is a continuation of similarly titled U.S. patent application Ser. No. 11/510,961 filed Aug. 28, 2006, now U.S. Pat. No. 7,270,158, which is a continuation of similarly titled U.S. patent application Ser. No. 11/070,440, filed Mar. 2, 2005; now U.S. Pat. No. 7,096,896, which, in turn, claims the benefit of U.S. Provisional Patent Application No. 60/550,805, filed Mar. 5, 2004, entitled "Apparatus for Needle Filling and Laser Resealing;" U.S. patent application Ser. No. 12/768,885, filed Apr. 28, 2010, entitled "Apparatus for Molding and Assembling Containers with Stoppers and Filling Same," now U.S. Pat. No. 7,975,453, which is a continuation of similarly titled U.S. patent application Ser. No. 11/074,513, filed Mar. 7, 2005, now U.S. Pat. No. 7,707,807, which claims the benefit of U.S. Provisional Patent Application No. 60/551,565, filed Mar. 8, 2004, entitled "Apparatus and Method For Molding and Assembling Containers With Stoppers and Filling Same;" U.S. patent application Ser. No. 13/396,053, filed Feb. 14, 2012, entitled "Method for Molding and Assembling Containers with Stopper and Filling Same," which is a continuation of similarly titled U.S. patent application Ser. No. 12/715,821, filed Mar. 2, 2010, entitled "Method for Molding and Assembling Containers with Stopper and Filling Same," now U.S. Pat. No. 8,112,972, which is a continuation of similarly titled U.S. patent application Ser. No. 11/074,454, filed Mar. 7, 2005, now U.S. Pat. No. 7,669,390; U.S. patent application Ser. No. 11/339,966, filed Jan. 25, 2006, entitled "Container Closure With Overlying Needle Penetrable and Thermally Resealable Portion and Underlying Portion Compatible With Fat Containing Liquid Product, and Related Method," now U.S. Pat. No. 7,954,521, which, in turn, claims the benefit of U.S. Provisional Patent Application No. 60/647,049, filed Jan. 25, 2005, entitled "Container with Needle Penetrable and Thermally Resealable Stopper, Snap-Ring, and Cap for Securing Stopper;" U.S. patent application Ser. No. 12/861,354, filed Aug. 23, 2010, entitled "Ready To Drink Container With Nipple and Needle Penetrable and Laser Resealable Portion, and Related Method;" which is a divisional of similarly titled U.S. patent application Ser. No. 11/786,206, filed Apr. 10, 2007, now U.S. Pat. No. 7,780,023, which, into turn, claims the benefit of similarly titled U.S. Provisional Patent Application No. 60/790,684, filed Apr. 10, 2006; U.S. patent application Ser. No. 11/295,251, filed Dec. 5, 2005, entitled "One-Way Valve, Apparatus and Method of Using the Valve," now U.S. Pat. No. 7,322,491, which, in turn, claims the benefit of similarly titled U.S. Provisional Patent Application No. 60/644,130, filed Jan. 14, 2005, and similarly titled U.S. Provisional Patent Application No. 60/633,332, filed Dec. 4, 2004; U.S. patent application Ser. No. 12/789,565, filed May 28, 2010, entitled "Resealable Containers and Methods of Making, Filling and Resealing the Same," which is a continuation of U.S. patent application Ser. No. 11/933,272, filed Oct. 31, 2007, entitled "Resealable Containers and Assemblies for Filling and Resealing Same," now U.S. Pat. No. 7,726,357, which is a continuation of U.S. patent application Ser. No. 11/515,162, filed Sep. 1, 2006, entitled "Sealed Containers and Methods of Making and Filling Same," now U.S. Pat. No. 7,726,352; U.S. patent application Ser. No. 13/045,655, filed Mar. 11, 2011, entitled "Sterile Filling Machine Having Filling Station and E-Beam Chamber," which is a continuation of U.S. patent application Ser. No. 12/496,985, filed Jul. 2, 2009, entitled "Sterile Filling Machine Having Needle Filling Station and Conveyor," now U.S. Pat. No. 7,905,257, which is a continuation of U.S. patent application Ser. No. 11/527,775, filed Sep. 25, 2006, entitled "Sterile Filling Machine Having Needle Filling Station within E-Beam Chamber," now U.S. Pat. No. 7,556,066, which is a continuation of similarly titled U.S. patent application Ser. No. 11/103,803, filed Apr. 11, 2005, now U.S. Pat. No. 7,111,649, which is a continuation of similarly titled U.S. patent application Ser. No. 10/600,525, filed Jun. 19, 2003, now U.S. Pat. No. 6,929,040, which, in turn, claims the benefit of similarly-titled U.S. Provisional Patent Application No. 60/390,212, filed Jun. 19, 2002; U.S. patent application Ser. No. 13/326,177, filed Dec. 14, 2011, entitled "Device with Penetrable and Resealable Portion and Related Method," which is a continuation of similarly titled U.S. patent application Ser. No. 13/170,613, filed Jun. 28, 2011, now U.S. Pat. No. 8,347,923, which is a continuation of U.S. patent application Ser. No. 12/401,567, filed Mar. 10, 2009, entitled "Device with Needle Penetrable and Laser Resealable Portion and Related Method," now U.S. Pat. No. 7,967,034, which is a continuation of similarly titled U.S. patent application Ser. No. 11/933,300, filed Oct. 31, 2007, now U.S. Pat. No. 7,500,498; U.S. patent application Ser. No. 13/329,483, filed Apr. 30, 2011, entitled "Ready to Feed Container," which is a continuation of International Application No. PCT/US2011/034703, filed Apr. 30, 2011, entitled "Ready to Feed Container and Method," which, in turn, claims the benefit of U.S. Provisional Patent Application No. 61/330,263 filed Apr. 30, 2010; and U.S. Provisional Patent Application No. 61/476,523, filed Apr. 18, 2011, entitled "Filling Needle and Method."

Alternatively, the septum 50 may be needle penetrated for sterile filling the variable-volume storage chamber and resealed with a liquid sealant, such as a silicone sealant, to hermetically seal the filled substance within the storage chamber, in accordance with the teachings of any of the following patent applications, each of which is hereby expressly incorporated by reference in its entirety as part of the present disclosure: U.S. patent application Ser. No. 12/577,126, filed Oct. 9, 2009, entitled "Device with Co-Extruded Body and Flexible Inner Bladder and Related Apparatus and Method," which claims the benefit of similarly titled U.S. Provisional Patent Application No. 61/104,613, filed Oct. 10, 2008; U.S. patent application Ser. No. 12/901,420, filed Oct. 8, 2010, entitled "Device with Co-Molded One-Way Valve and Variable Volume Storage Chamber and Related Method," which claims the benefit of similarly titled U.S. Provisional Patent Application No. 61/250,363, filed Oct. 9, 2009; and U.S. Provisional Patent Application No. 61/476,523, filed Apr. 18, 2011, entitled "Filling Needle and Method."

Prior to filling the variable-volume storage chamber 48, the sealed empty chamber may be sterilized by injecting a fluid sterilant therein, such as nitric oxide, with a needle, filling or injection member through the penetrable and resealable septum 50, and the needle employed for injecting the fluid sterilant and/or the substance to be sterile filled into the variable-volume storage chamber may be a self opening and closing needle, in accordance with the teachings of any of the following co-pending patent applications, each of which is hereby expressly incorporated by reference in its entirety as part of the present disclosure: U.S. patent application Ser. No. 13/450,306, filed Apr. 18, 2012, entitled "Needle with Closure and Method," which claims the benefit of U.S. Provisional Patent Application No. 61/476,523, filed Apr. 18, 2011, entitled "Filling Needle and Method;" and U.S. patent application Ser. No. 13/529,951, filed Jun. 21, 2012, entitled "Fluid Sterilant Injection Sterilization Device and Method," which claims the benefit of U.S. Provisional Patent Application No. 61/499,626, filed Jun. 21, 2011, entitled "Nitric Oxide Injection Sterilization Device and Method." As may be recognized by those of ordinary skill in the pertinent art based on the teachings herein, the penetrable and resealable septum may be penetrated and resealed, and the variable-volume storage chamber may be sterilized and sterile filled, by any of numerous different devices and methods that are currently known, or that later become known.

Figure 2:
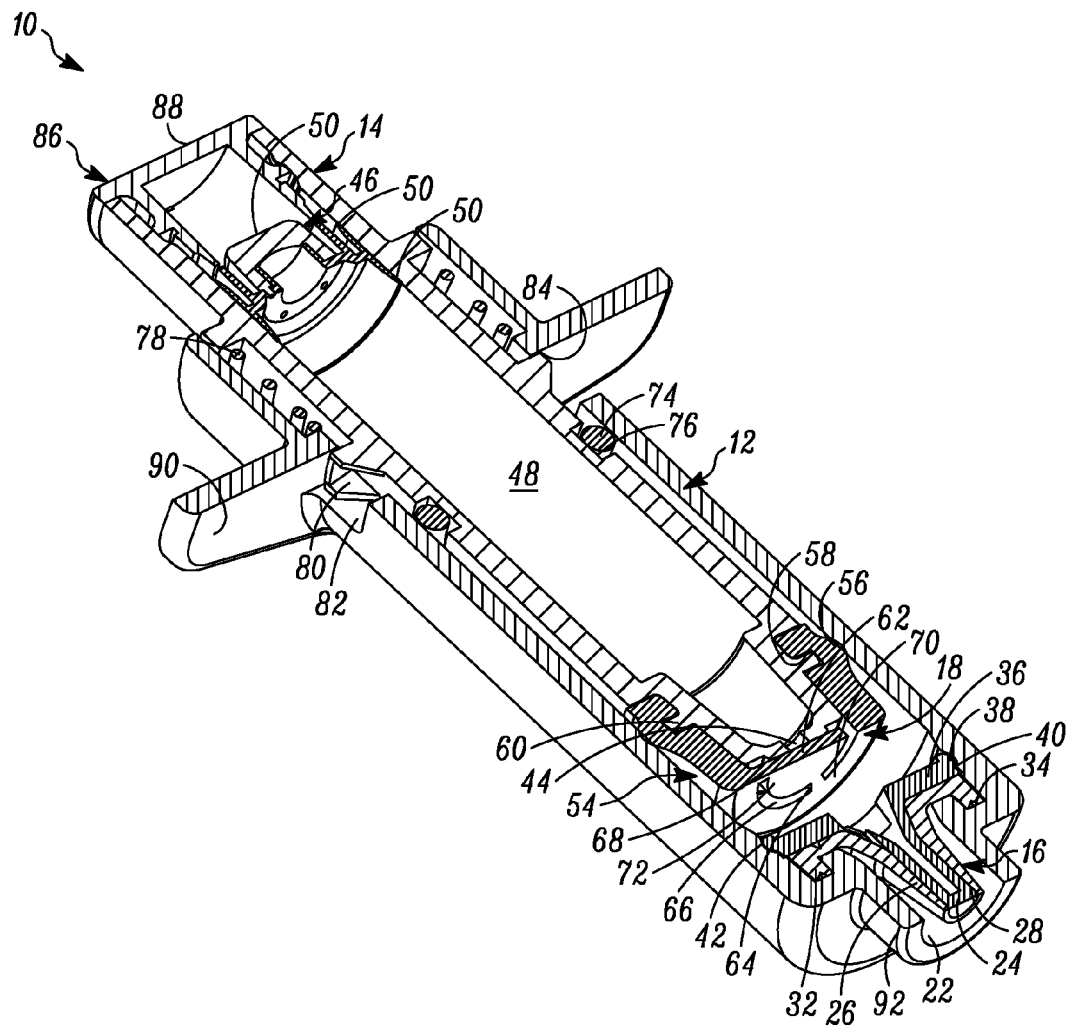
FIG. 2 is a perspective cross-sectional view of the syringe of FIG. 1.

The plunger 14 includes an elastomeric tip 54 that defines on the distal end thereof the second valve 18, and on a proximal portion thereof a primary laterally-extending annular seal 56 that laterally extends annularly about the plunger tip 54 and forms a sliding, fluid-tight seal between the plunger tip 54 and the interior surface of the body 12. As shown in FIGS. 1-4, the primary annular seal 56 forms an interference fit with the substantially cylindrical interior surfaces of the syringe body 12 and thereby forms a fluid-tight seal therebetween (and thus between the proximal end of the compression chamber 20 and ambient atmosphere). The plunger tip 54 defines an inner laterally-extending annular groove 58 for receiving therein a corresponding laterally-extending annular retaining member 60 of the plunger 14 to fixedly secure the plunger tip 54 thereto. The second valve 18 includes an elastic second valve member 62 formed on the distal end of the plunger tip 54 and overlying the storage chamber outlet 44. The second valve 18 further includes a plurality of elastic valve connecting members 64 extending radially between the second valve member 62 and the peripheral portion of the plunger tip 54. As best shown in FIG. 2, the elastic valve connecting members 64 are angularly spaced relative to each other and define angularly extending flow apertures 66 therebetween. In the illustrated embodiment, the second valve 18 includes three valve connecting members 64 substantially equally angularly spaced relative to each other and defining three flow apertures 66 therebetween. However, as may be recognized by those of ordinary skill in the pertinent art based on the teachings herein, this number of valve connectors and flow apertures is only exemplary and may be changed as desired or otherwise to meet the requirements of a particular application or configuration. The second valve 18 further includes a second valve seat 68 defined by a distal surface of the plunger 14 extending about the periphery of the storage chamber outlet 44. The elastic valve connecting members 64 normally bias the second valve member 62 into engagement with the second valve seat 68 to thereby form a normally-closed second valve seam 70 therebetween. In the normally-closed position, as shown in FIGS. 1-4, a fluid-tight seal is formed at the valve seam 70 between the second valve member 62 and second valve seat 68 to thereby prevent the flow of fluid through the second valve 18. However, when the pressure differential across the second valve 18 exceeds a second valve opening pressure, the second valve member 62 is moved distally against the bias of the elastic valve connecting members 64 and relative to the second valve seat 68, to thereby open the second valve seam 70 and define a valve opening at the seam to, in turn, allow a dose of substance to flow from the variable-volume storage chamber 48, through the second valve opening 44, and into the compression chamber 20. In the illustrated embodiment, the second valve opening pressure is set by selecting the elastic properties of the second valve member 62 and valve connecting members 64 and/or the number of valve connecting members. In the illustrated embodiment, the elastic material defines a shore hardness within the range of about 50 to about 70 shore A. As may be recognized by those of ordinary skill in the pertinent art based on the teachings herein, the second valve may be any of numerous different one-way valves, that are currently known, or that later become known, for performing the function of the second valve as described herein, including without limitation a check valve, a duckbill valve, a flapper valve or an umbrella valve.

As best shown in FIG. 2, the plunger 14 further defines a compression surface 72 formed by the distal surfaces of the plunger tip 54 and second valve member 62. The compression chamber 20 is formed between the compression surface 72 and the first valve 16. Movement of the compression surface 72 when the plunger 14 is displaced between first and second positions creates pressure differentials across both the first and second valves 16 and 18, respectively, resulting in the dispensing of a dose of substance within the compression chamber 20 through the first valve 16 and out of the syringe 10, and the releasing of another dose of the substance from the variable-volume storage chamber 48 through the second valve 18 and into the compression chamber 20, as described further below.

The syringe 10 further includes a secondary or environmental seal 74 formed between the plunger 14 and the body 12 and proximally spaced relative to the primary seal 56. The secondary seal 74 is received within an annular recess 76 formed in the outer side wall of the plunger 14. As shown in FIGS. 1-4, the secondary seal 74 forms an interference fit with the interior surface of the syringe body 12 to thereby form a substantially fluid-tight seal therebetween. The secondary seal 74 substantially prevents contaminants from passing distally therethrough and, in turn, maintains the proximal interior surfaces of the syringe body 12 that contact the primary seal 56 sterile, aseptic and/or otherwise substantially contaminant free. The primary and secondary seals may be formed integral to the plunger 14 and/or the plunger elastomeric tip 54, such as by forming thereon annular protuberances. Alternatively, they may be formed by sealing members, such as o-rings or other sealing members, that are received within corresponding grooves or recesses formed in the plunger 14, extending annularly about the plunger. The primary seal 56 and the first valve 16 seal off the compression chamber 20 with respect to ambient atmosphere, while allowing sliding movement of the plunger 14 and/or the body 12 relative to the other between the first and second positions. The secondary seal 74, spaced proximally from the primary seal 56, seals off the primary seal and the portions of the plunger 14 and/or the body 12 contacted by the primary seal, with respect to ambient atmosphere.

As shown in FIGS. 1-4, the syringe 10 further includes a spring 78 coupled between the plunger 14 and the body 12. The spring 78 normally biases the plunger 14 from the second position, wherein the compression surface 72 is closer to the first valve 16, to the first position, wherein the compression surface is farther away from the first valve. However, as may be recognized by those of ordinary skill in the pertinent art based on the teachings herein, the plunger 14 may be biased in any of numerous different ways that are currently known, or that later become known, and if a spring is used, any of numerous different springs or combinations of springs may be used, including without limitation, a coil spring, and an elastic spring, such as of the type described further below.

The plunger 14 includes a stop member 80 projecting radially therefrom, and the body 12 defines a corresponding groove or aperture 82 for receiving the stop member 80. The aperture 82 defines a stop surface 84 which engages the stop member 80 when the plunger 14 is in the normally biased first position, and prevents further proximal movement of the plunger relative to the body. As may be recognized by those of ordinary skill in the pertinent art based on the teachings herein, the plunger and the syringe body may utilize any of numerous different devices or methods that are currently known, or that later become known, to control and/or otherwise limit movement of the plunger and/or syringe body relative to the other between first and second positions.

The plunger 14 further includes a cap 86 that is received within and encloses the proximal end of the plunger. The cap 86 defines a first manually-engageable surface 88 for depressing the plunger 14. After filling the variable-volume storage chamber 48 through the penetrable and resealable septum 50, the cap 86 is inserted into the opening in the proximal end of the plunger to protectively cover the open end and provide the manually-engageable surface 88 for actuating the plunger 14. As shown typically in FIG. 3, when attached to the proximal end of the plunger 14, a depending flange 87 of the cap 86 engages the peripheral surfaces of the tabbed ends 55 of the legs 53 of the sliding seal 46. As the cap 86 is pressed into the open end of the plunger 14, the depending flange 87 deforms the legs 53 of the sliding seal 46 radially inwardly and away from contact with the interior wall of the plunger 14 and the tabbed ends from the proximal end of the plunger 14. This, in turn, allows that sliding seal 46 to move axially within the plunger 14 and thereby accommodate reductions in the volume of the storage chamber 48 upon dispensing doses of the stored substance therefrom. As shown in FIG. 3, the plunger 14 defines a tapered protuberance 89 formed adjacent to the proximal end of the plunger 14. As can be seen, the tapered protuberance 89 defines a tapered surface on the proximal side thereof to allow the distal end of the depending rim 89 of the cap 86 to slide over the tapered protuberance 89 when assembling the cap 86 to the plunger 14, but to prevent removal of the cap 86 from the plunger 14 once snap fit or otherwise received within the distal side of the tapered protuberance 89. As shown in FIG. 3, the cap 86 includes one or more vent apertures 91 to prevent the formation of a vacuum between the sliding seal 46 and the cap 86, and otherwise to allow the sliding seal 46 to travel through the plunger 14 upon dispensing the substance from the storage chamber 48.

The body 12 also includes a second manually-engageable surface 90 projecting radially therefrom to allow a user to grip the body 12 with the same hand used to manually depress the plunger 14 from the first position to the second position. In one mode of operation, a user grips the second manually-engageable surface 90 with the index and middle finger of the same hand, and engages the first manually-engageable surface 88 with the thumb of the same hand, to depress the plunger 14 from the first position toward the second position by squeezing the thumb toward the index and middle fingers. After dispensing a dose, the thumb is released from the first manually-engageable surface 88 (or the thumb may touch but no longer apply pressure to the first manually-engageable surface) to allow the spring 78 to drive the plunger 14 from the second position back into the first position and ready the device to dispense another dose.

In the first position, the volume of the compression chamber 20 corresponds approximately to the volume of a respective dose of substance to be dispensed through the first valve 16. When the plunger 14, and thus the compression surface 72, is depressed from the first position toward the second position, the dosage of substance within the compression chamber 20 is pressurized to a pressure exceeding the first valve opening pressure. Consequently, the first valve 16 opens, such that the first valve member 26 expands, e.g., radially, away from the first valve seat 24 (or axially spaced segments of the valve member 26 progressively radially expand and close as the dose moves through the axially-elongated valve seam 28), and the respective dose of substance in the compression chamber 20 is dispensed through the first valve seam 28 and out of the syringe 10. Thereafter, the first valve 16 (or all segments or substantially all segments of the valve member 26) returns to the normally closed position. As described above, the first valve 16 only allows the flow of substance in a direction exiting the body 12, and prevents an ingress of germs, bacteria or other unwanted substances through the valve and into the compression chamber 20 and otherwise into the interior of the body 12.

When the plunger 14 is released, the spring 78 naturally biases, rebounds and/or returns the plunger 14 from the second position toward the first position, thereby creating a partial vacuum in the compression chamber 20. The partial vacuum creates a pressure differential across the second valve 18 exceeding the second valve opening pressure. Consequently, the second valve 18 opens and another dosage of the substance in the variable-volume storage chamber 48 is released into the compression chamber 20. While the respective dose of substance is released from the storage chamber 48, suction forces exerted on the sliding seal 46 caused by the exit of the substance from the storage chamber 48 cause the seal to move distally within the plunger 14 to correspondingly reduce the volume of the storage chamber 48. Once the compression chamber 20 is refilled with another dose of substance, and/or the pressure differential across the second valve 18 falls below the second valve opening pressure, the second valve returns to its normally closed position to seal the outlet 44 of the variable-volume storage chamber 48.

The body 12 further comprises a connector 92 located adjacent to the first valve 16, at the distal end of the body, adapted to connect an administering member thereto for administering the dispensed dose of substance to a patient, such as by parenteral or enteral administration. As may be recognized by those of ordinary skill in the pertinent art based on the teachings herein, the connector may be any of numerous different connectors that are currently known, or that later become known, for performing the function of the connector as described herein, including a luer connector. As also may be recognized by those of ordinary skill in the pertinent art based on the teachings herein, the administering member may be any of numerous different administering members that are currently known, or that later become known, for performing the function of the member as described herein, including a disposable needle for parenteral administration or a shield for nasal or oral administration.

Figure 5:
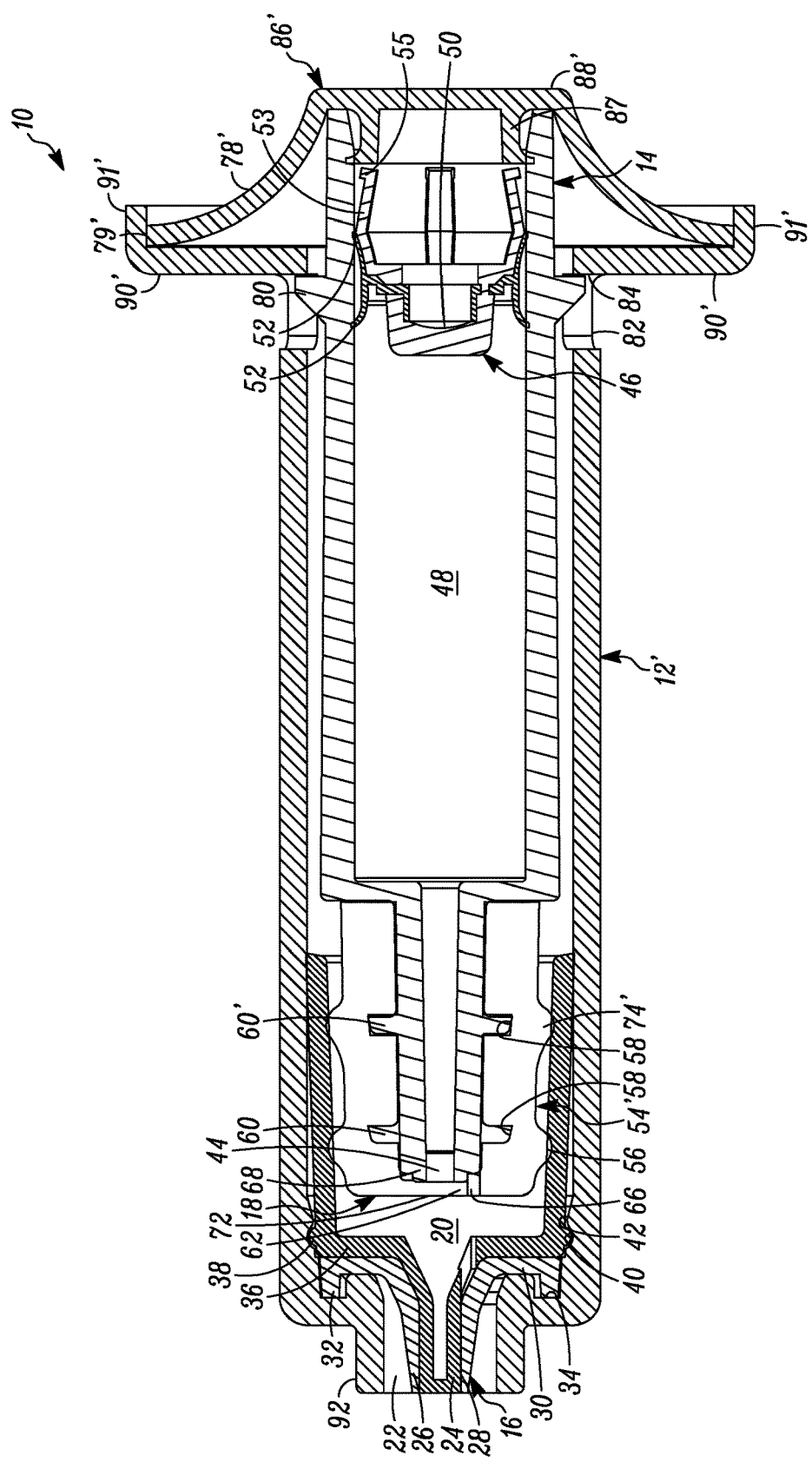
FIG. 5 is a cross-sectional view of another embodiment of a multiple dose syringe including an elastic spring for normally biasing the plunger in the direction from the second position toward the first position.

In FIG. 5, another device is indicated generally by the reference numeral 10. The device 10 of FIG. 5 is substantially the same as the device 10 described above in connection with FIGS. 1-4, and therefore like reference numerals are used to indicate like elements. Elements of the embodiment of FIG. 5 that differ from the corresponding elements of the embodiment of FIGS. 1-4 are indicated with a prime symbol, e.g., 12', 60', 74', 78', 86', 88' and 90'. The primary difference of the device 10 of FIG. 5 in comparison to the device 10 of FIGS. 1-4, is that the device 10 of FIG. 5 includes an elastic spring 78', instead of a coil spring, that normally biases the plunger 14 in the direction from the second position toward the first position. As shown in FIG. 5, the elastic spring 78' is formed integral with the end cap 86' of the plunger 14. The manually-engageable surface 90' extends annularly about the proximal end of the syringe body 12 and includes a proximally-directed peripheral rim 91'. The elastic spring 78' also extends annularly about the cap 86' and syringe body 12' and defines a distal peripheral edge 79' that resiliently engages the peripheral rim 91' of the manually-engageable surface 90'. As shown in FIG. 5, the elastic spring 78' is curved inwardly toward the plunger 14 between the manually-engageable surface 88' and the distal peripheral edge 79'. Accordingly, when the manually-engageable surface 88 is depressed to move the plunger 14 from the first position toward the second position, the elastic spring 78' is deflected and compressed such that in the second position the deflected and compressed portion of the spring retains a sufficient spring force to drive the plunger 14 from the second position into the first position, and create a pressure differential across the second valve 18 that exceeds the second valve opening pressure. As also shown in FIG. 5, the secondary seal 74' is defined by a second laterally-extending annular protuberance of the elastomeric plunger tip 54' spaced proximally relative to the primary laterally-extending annular seal 56. As may be recognized by those of ordinary skill in the pertinent art based on the teachings herein, the elastic spring may take the form of any of numerous different types of elastic springs, and may be connected between, or otherwise may bias the plunger in the direction from the second position toward the first position, in any of numerous different ways, that are currently known, or that later become known. For example, as described below, the elastic spring may take the form of an approximately dome-shaped spring, and the dome-shaped spring may, if desired, form the compression chamber.

In FIGS. 7-13, another device is indicated generally by the reference numeral 110. The device 110 is substantially similar to the device 10 described above in connection with FIGS. 1-6B, and therefore like reference numerals preceded by the numeral "1" are used to indicate like elements. A primary difference of the device 110 in comparison to the device 10 is that the variable-volume storage chamber 148 is located external of the syringe body 112, is connected to the compression chamber 120 through a conduit 194, and the compression chamber is defined by a substantially dome-shaped or other type of elastomeric spring 178, as hereinafter described.

Figure 7:
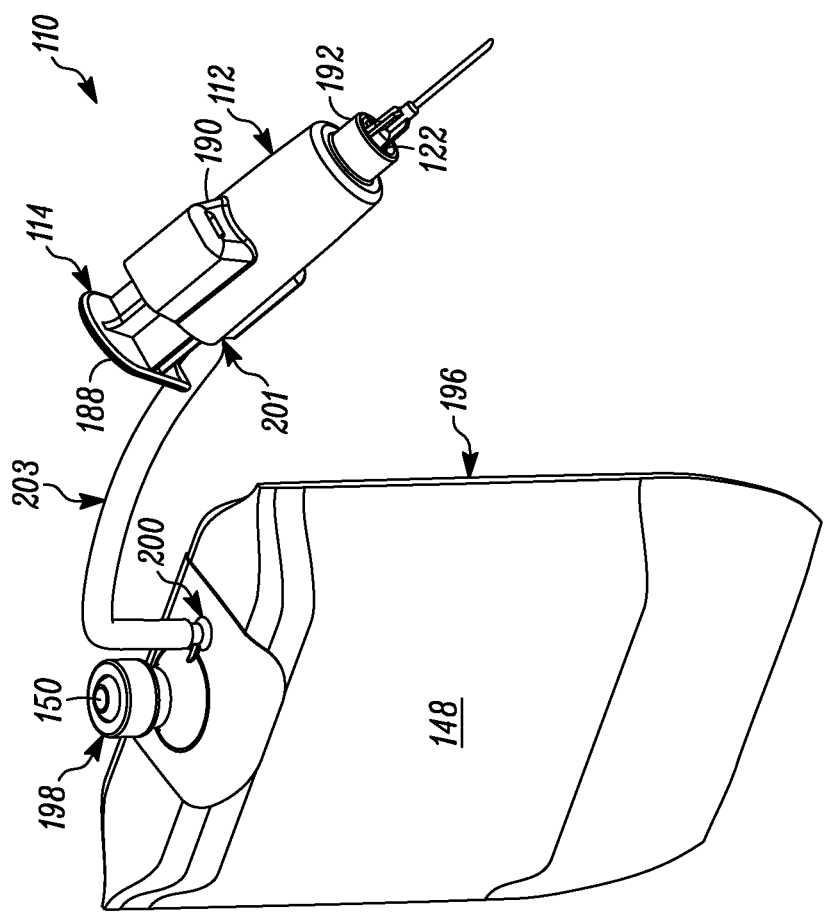
FIG. 7 is a perspective view of another embodiment of a syringe wherein the variable-volume storage chamber is defined by an external pouch connected to the compression chamber of the syringe through flexible tubing.
Figure 8:
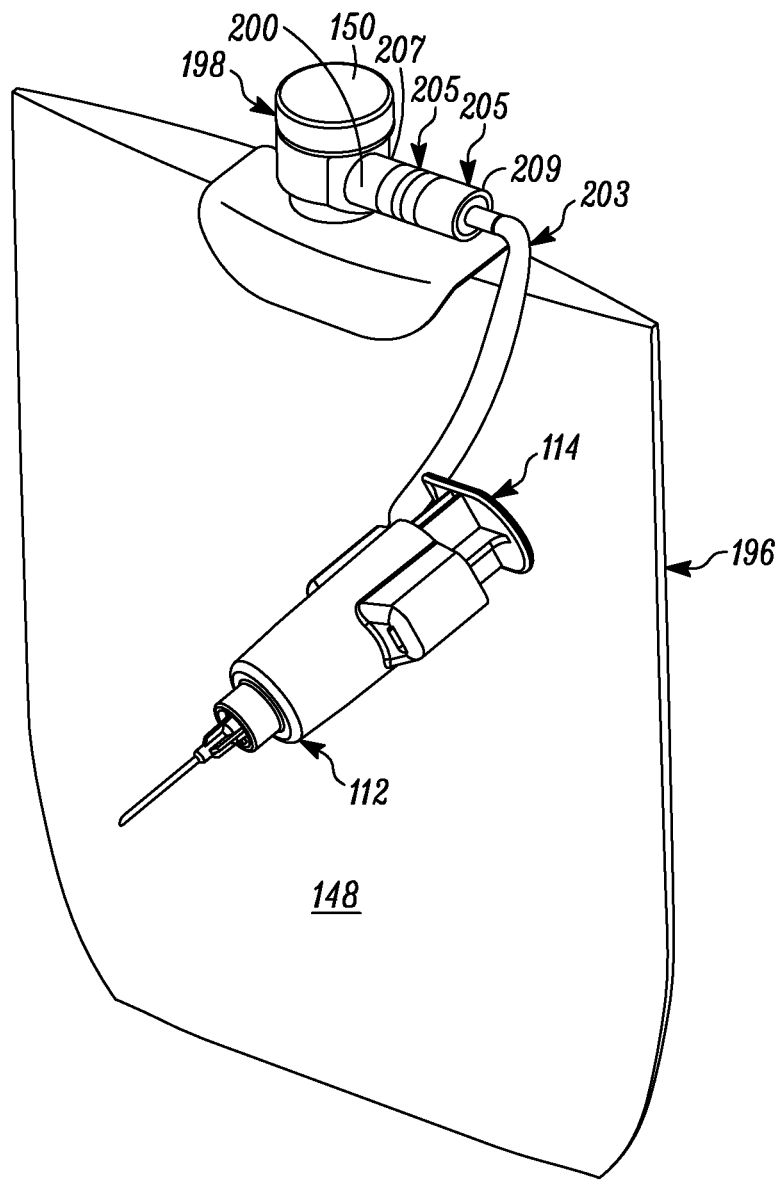
FIG. 8 is a perspective view of the syringe of FIG. 7 wherein the variable-volume storage chamber is connected to the compression chamber of the syringe via a sterile connector.
Figure 9:
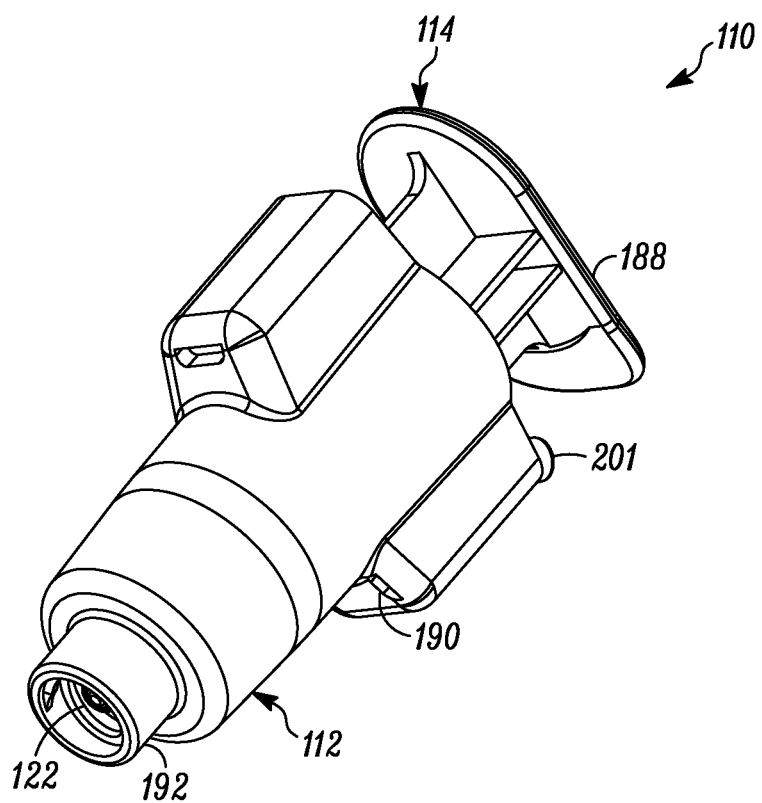
FIG. 9 is a side perspective view of the syringe of FIG. 7.
Figure 10:
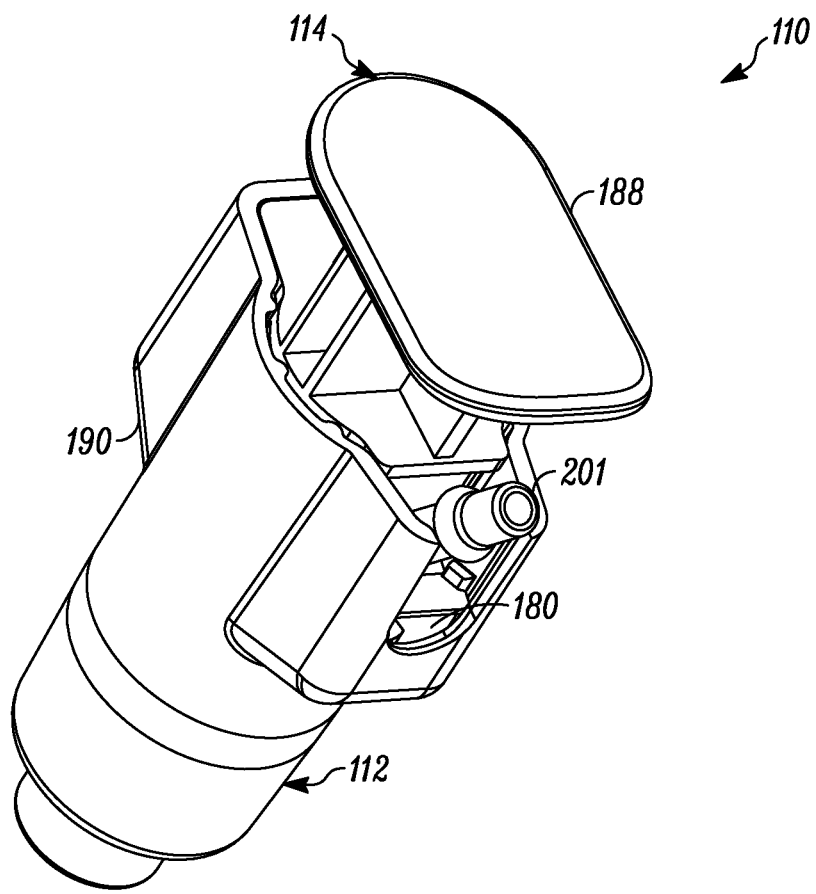
FIG. 10 is a proximal perspective view of the syringe of FIG. 7.

As shown in FIG. 7, the variable-volume storage chamber 148 is defined by a bladder, bag, or pouch 196, having a filling port 198 and an outlet port 200. Similar to the embodiment described above in connection with FIGS. 1-6B, the filling port 198 includes a penetrable and resealable septum 150 that is penetrable by a needle, filling or injection member (not shown) for sterile or aseptically filling the storage chamber 148 with multiple doses of the substance to be stored therein. The septum 150 can be formed of a material that is sufficiently elastic to close itself after withdrawal of the needle or other injection member therefrom to thereby ensure that the head loss left by a residual penetration hole after the injection member is withdrawn prevents fluid ingress therethrough. Although the septum 150 is self-closing, the septum may be resealed by liquid sealant such as silicone or a silicone-based sealant, and/or the application of radiation or energy thereto to hermetically seal the substance within the storage chamber 148 from the ambient atmosphere and thereby maintain the sterility of the substance. The septum 150 may be penetrable for sterile filling the variable-volume storage chamber and resealable, e.g., laser releasable, to hermetically seal the filled substance within the storage chamber in accordance with the teachings of any of the patents and patent applications incorporated by reference above. Alternatively, the septum 150 may be penetrable for sterile filling the variable-volume storage chamber, and resealable with a liquid sealant, such as a silicone sealant, to hermetically seal the filled substance within the storage chamber, in accordance with the teachings of any of the patents and patent applications incorporated by reference above.

As shown in FIGS. 10-13, the plunger 114 of the syringe 110 includes an inlet conduit 194 defining an inlet port 201 on one end thereof and an outlet in fluid communication with an inlet 170 of the second valve 118. A flexible tube 203 is connected at an inlet end thereof to the outlet port 200 of the variable-volume storage chamber 148, and is connected at an outlet end thereof to the inlet port 201 of the plunger conduit 194. As shown typically in FIG. 8, a sterile connector 205 may be utilized to form a sterile or aseptic connection between the outlet port 200 of the variable-volume storage chamber 148 and the flexible tube 203 connected to the inlet port 201 of the syringe plunger. The sterile connector 205 may allow for the connection of multiple storage chambers 148 to a respective syringe 110, and/or for connecting multiple syringes 110 to a respective storage chamber 148, while maintaining the sterile, aseptic or contamination-free condition of the substance within a respective syringe and storage chamber. Alternatively, the sterile connector 205 may be configured to allow a sterile connection between the male and female sides of the connector, but to prevent (or substantially prevent) their disconnection, such as by forming a snap fit or other type of locking connection between the male and female sides of the connector. This type of locking sterile connector may be desirable to prevent connecting different pouches or other types of variable-volume storage chambers to the same syringe, such as when the different pouches contain different medicaments or other substances that could cross-contaminate each other.

The sterile connector 205 comprises a first or male connector 207 that is connectable to a second or female connector 209. The first and second connectors 207 and 209, respectively, each include a normally-closed one-way valve preventing exposure of the substance within the storage chamber 148 and the interior of the syringe 110 to the ambient atmosphere. When the connectors are connected to one another, the respective one-way valves are opened, thereby allowing an aseptic or sterile flow of fluid or other stored substance therethrough from the storage chamber to the syringe. Upon disconnection of the first and second connectors 207 and 209, respectively, the one-way valves return to their normally closed state, thereby preserving the sterility of the substance within the storage chamber 148 and the sterility of the interior of the syringe 110. The sterile connector 205 may be the same as, or substantially similar to, any of the sterile connectors disclosed in any of the following co-pending patent applications, each of which is hereby expressly incorporated by reference in its entirety as part of the present disclosure: U.S. patent application Ser. No. 13/080,537, filed Apr. 5, 2011, entitled "Aseptic Connector with Deflectable Ring of Concern and Method," which, in turn, claims the benefit of similarly titled U.S. Provisional Application No. 61/320,857, filed Apr. 5, 2011. However, as may be recognized by those of ordinary skill in the pertinent art based on the teachings herein, any of numerous different sterile or aseptic connectors that are currently known, or that later become known, may be utilized. For example, the sterile connector 205 may be the same as, or substantially similar to, any of the sterile connectors disclosed in any of the following co-pending provisional patent applications, each of which is hereby expressly incorporated by reference in its entirety as part of the present disclosure: U.S. Provisional Patent Application No. 61/625,663, filed Apr. 17, 2012, entitled "Self Closing Connector," similarly titled U.S. Provisional Patent Application No. 61/635,258, filed Apr. 18, 2012, and U.S. Provisional Patent Application No. 61/641,248, filed May 1, 2012, entitled "Device for Connecting or Filling and Method." In addition, the device may include more than one sterile connector and the sterile connector may be placed between the variable-volume storage chamber and the flexible tube, as part of the flexible tube, between the flexible tube and the syringe, or at any of other numerous different connection points. For example, the device may include a first sterile connector at the inlet to the syringe, plunger or compression chamber of the syringe, and another sterile connector at the outlet of the variable-volume storage chamber. Still further, the variable-volume storage chamber may be aseptically or sterile filled through a sterile connector.

Figure 11:
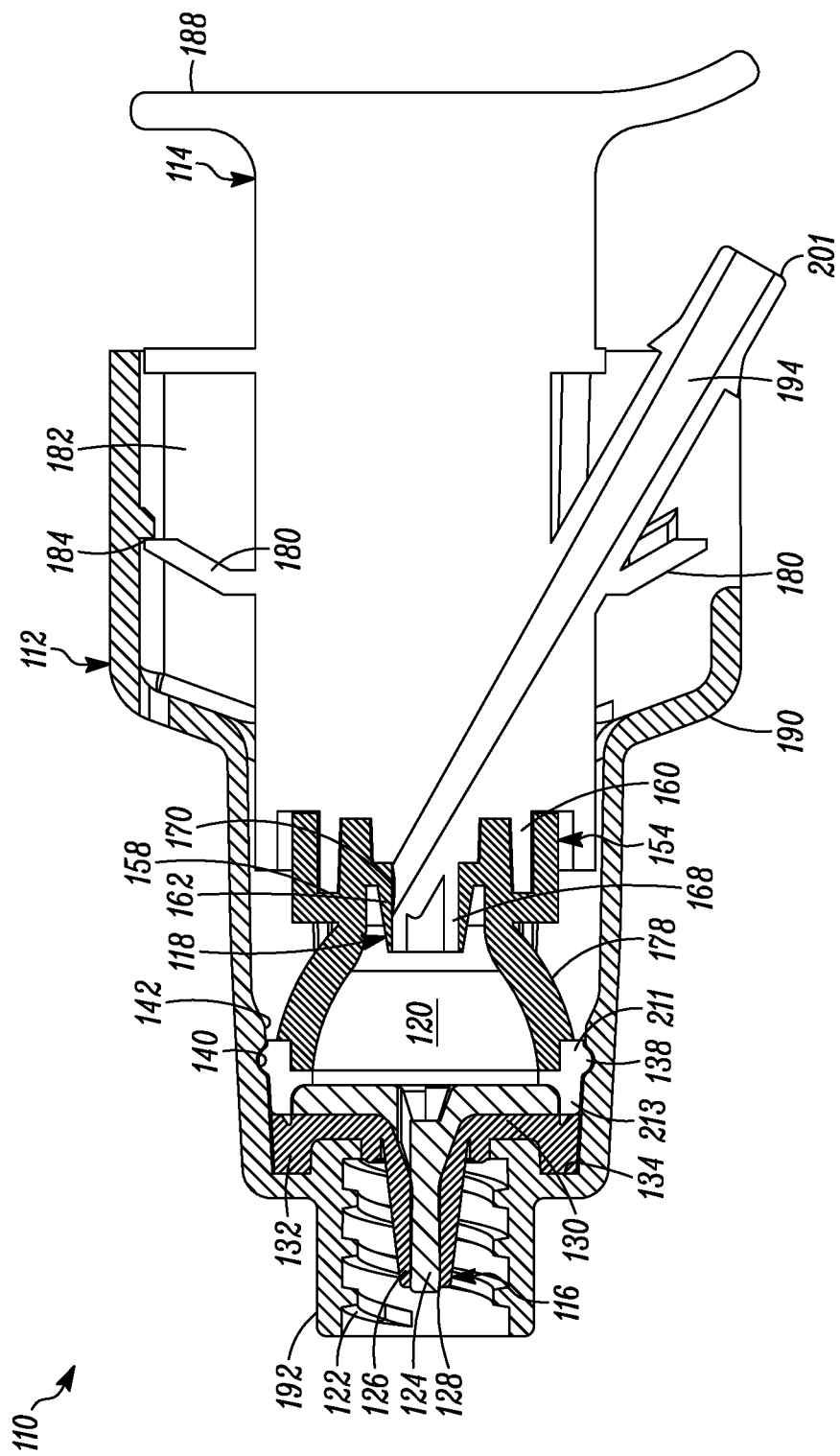
FIG. 11 is a cross-sectional view of the syringe of FIG. 7 showing the plunger in a first or unactuated position.
Figure 12:
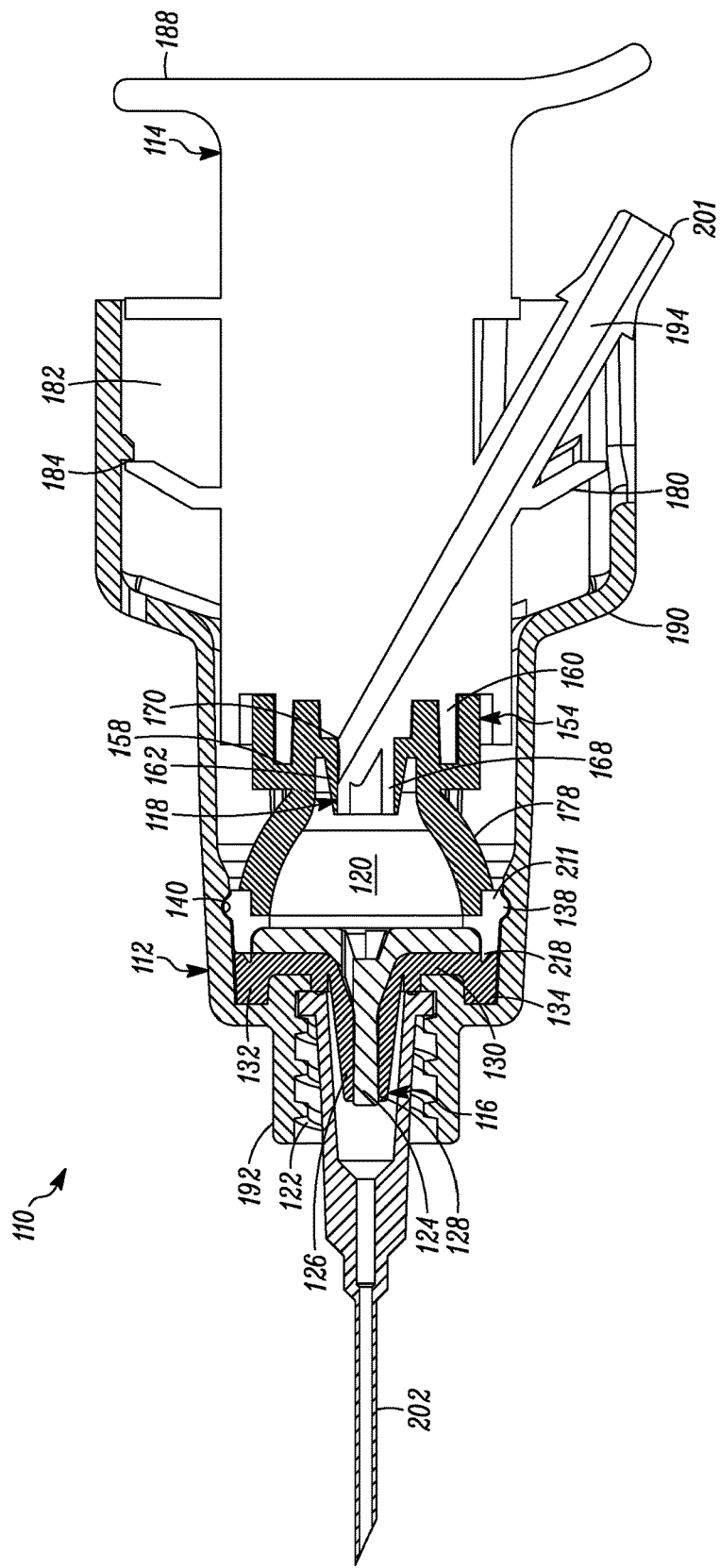
FIG. 12 is a cross-sectional view of the syringe of FIG. 7 showing a needle connected via a luer fitting to the outlet of the syringe and the syringe plunger in the first or unactuated position.
Figure 13:
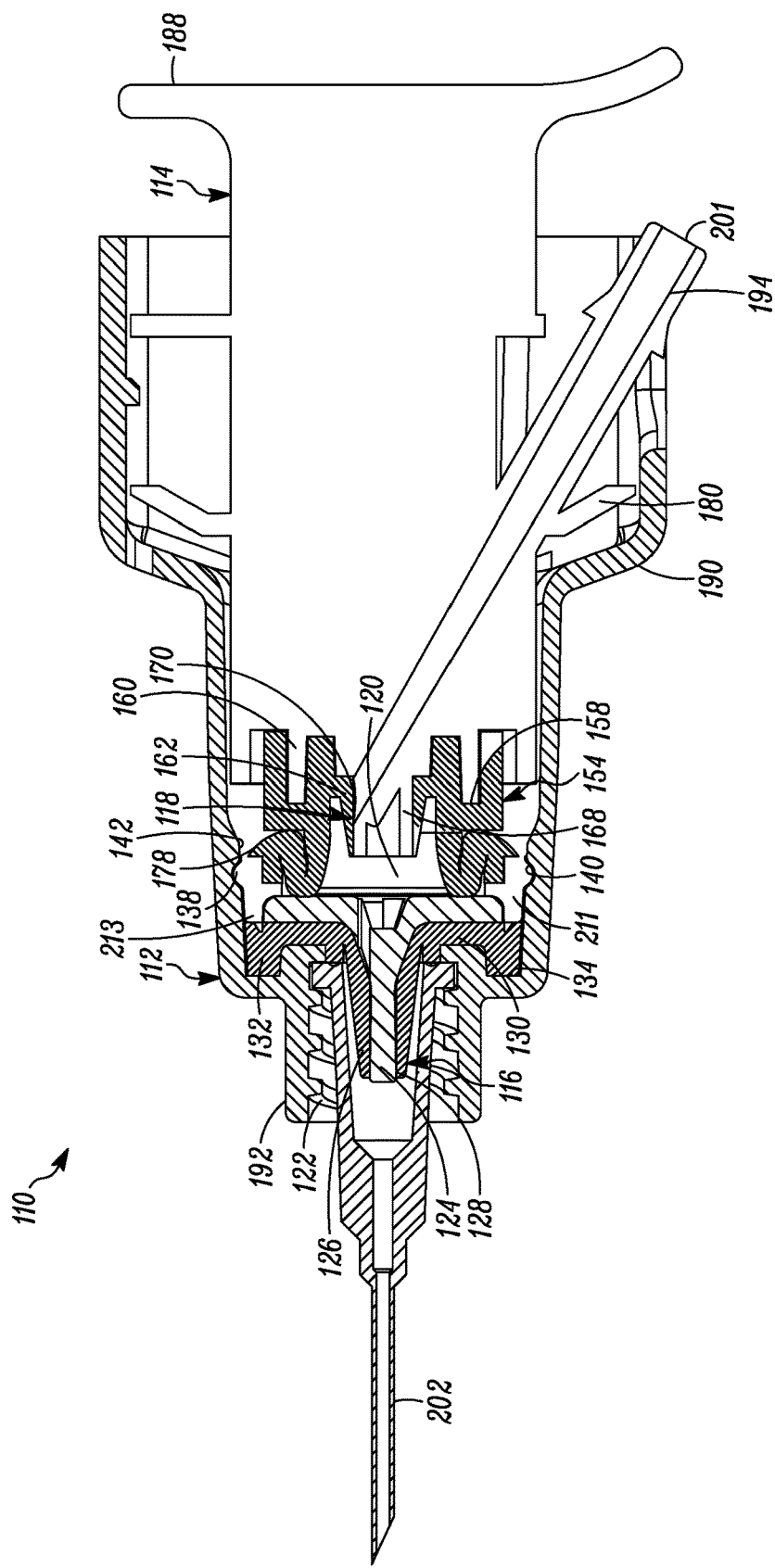
FIG. 13 is a cross-sectional view of the syringe of FIG. 12 showing the plunger in a second or actuated position.

As shown in FIGS. 11-13, the distal end of the plunger 114 defines the relatively rigid second valve seat 168 and a proximal end of the elastomeric plunger tip 154 defines the flexible second valve member or cover 162, mounted over and surrounding the second valve seat. The second valve member 162 and the second valve seat 168 define the axially-elongated, annular second valve seam 170 therebetween. The second valve member 162 can form an interference fit with the second valve seat 168 to thereby form a fluid-tight seal in a normally closed position and, in turn, maintain the substance within the compression chamber 120 in a sterile, aseptic and/or contamination free and hermetically sealed condition. The second valve 118 defines a second valve opening pressure, and remains in the normally closed position unless a pressure differential across the second valve 118 exceeds the second valve opening pressure. As shown in FIGS. 11-13, the second valve member 162 defines a substantially tapered cross-sectional shape moving in the axial direction from the inlet towards the outlet of the second valve seam 170. This configuration requires progressively less energy to open each respective annular portion of the valve when moving axially from the interior toward the exterior of the valve. Alternatively, or in combination with the tapered second valve member 162, the second valve seat 168 may define an outer diameter that progressively or otherwise increases in the axial direction from the inlet towards the outlet of the second valve seam, to provide the same or similar effect. As a result, once the base of the valve is opened, the pressure is sufficient to cause the downstream segments or portions of the second valve member 162 to progressively open and then close after passage of substance through the respective portion of the second valve seam 170 when moving in the direction from the plunger side towards the compression side of the second valve seam 170 to release the dosage of substance into the compression chamber 120.

The elastomeric plunger tip 154, and thus the second valve member 162, are formed integral with an approximately dome-shaped elastomeric spring 178. The elastomeric plunger tip 154 further defines, at the proximal end thereof, an inner annular axially-extending groove 158 which receives a corresponding annular axially-extending retaining member 160, defined by the distal end of the plunger 114, to fixedly secure the plunger tip 154 to the plunger 114.

The approximately dome-shaped elastic spring 178, which can be formed integral with the elastomeric plunger tip 154 at its proximal end as described above, includes a relatively rigid annular base 211 at its distal end, and normally biases the plunger 114 from the second, actuated position, as shown in FIG. 13, toward the first, unactuated position, as shown in FIG. 12. The annular base defines a laterally-extending annular protuberance 138 received within a corresponding annular recess 140 formed in the side wall of the syringe body 112. Distally adjacent thereto, an annular distal end 213 of the annular base 211 engages a proximal end of the first valve member base 130. When the annular protuberance 138 is received within the corresponding annular recess 140 of the syringe body 112, the annular distal end 213 of the annular base 211 compresses the first valve member base 130 to thereby form a fluid tight seal between the elastic spring 178 and the first one-way valve 116. As shown in FIG. 11, the syringe body 112 defines a tapered protuberance 142 formed proximally adjacent to the annular recess 140. As can be seen, the tapered protuberance 142 defines a tapered surface on the proximal side thereof to allow the annular protuberance 138 to slide over the tapered protuberance 142 when assembling the elastic spring 178 to engage the first valve member base 130, but to prevent removal of the elastic spring 178 from the syringe body 112 once snap fit or otherwise received within the annular recess 140 of the syringe body. In the illustrated embodiment, the annular base 211 is co-molded with the dome-shaped spring 178, such as by over-molding the elastic dome-shaped spring to the annular base.

As best shown in FIGS. 11 and 12, the compression chamber 120 is defined within the interior of the dome-shaped spring 178 and extends between the inlet of the first valve 116 and the outlet of the second valve 118. The dome-shaped spring 178, in cooperation with the first valve 116, seals the substance within the compression chamber 120 from the ambient atmosphere. When the plunger 114 is depressed from the first position (FIGS. 11 and 12) toward the second position (FIG. 13), the dome-shaped spring 178 is compressed, thereby pressurizing the substance within the compression chamber 120 to a pressure exceeding the valve opening pressure of the first valve 116 and dispensing the substance out of the syringe, in the same manner as described above in connection with the embodiment of FIGS. 1-6B. When the plunger 114 is released, the integral elastic spring 178 naturally rebounds and returns the plunger 114 from the second position toward the first position, thereby creating a partial vacuum in the compression chamber 120, in the same manner as described above in connection with the embodiment of FIGS. 1-6B. The partial vacuum created in the compression chamber 120 creates a pressure differential across the second valve 118 exceeding the second valve opening pressure. The resulting suction force causes another dosage of the substance in the variable-volume storage chamber 148 to flow through the conduit 194 and the second valve seam 170 of the second valve 118 and, in turn, into the compression chamber 120.

The plunger 114 includes a pair of laterally-extending wings 180 located on diametrically opposite sides of the plunger and projecting radially therefrom. As shown in FIGS. 11-13, the wings 180 are slidably received within corresponding wing-receiving grooves 182 in the syringe body 112. Within the grooves 182, respective stop surfaces 184 are defined by protuberances extending inwardly from the inner surface of the body sidewall. The stop surfaces 184 engage the wings 180 when the plunger 114 is in the normally biased first position, and prevent further proximal movement of the plunger relative to the body. As may be recognized by those of ordinary skill in the pertinent art based on the teachings herein, the plunger and the syringe body may utilize any of numerous different devices or methods that are currently known, or that later become known, to control and otherwise limit movement of the plunger and/or syringe body relative to the other between first and second positions. The proximal end of the plunger 114 further defines a first manually-engageable surface 188 for depressing the plunger 114. The grooves 182 each define respective second manually-engageable surfaces 190 along their distal ends, to allow a user to grip with index and middle fingers, the body 112, and manually depress the plunger 114 from the first position toward the second position with a thumb of the same hand.

As shown in FIGS. 12 and 13, in the illustrated embodiment, a needle 202 is connectible to the connector 192 at the outlet 122 of the syringe 110. The needle 202 includes a male luer connector, and the connector 192 includes a female luer connector, to provide a quick connect and disconnect, and fluid-tight connection between the needle and syringe. As can be seen, each dosage of substance dispensed through the first valve 116 is injected through the interior of the needle 202 and into a patient penetrated by the needle. In the illustrated embodiment, each dose is pressurized in the compression chamber 120 to, in turn, impart sufficient velocity to the dose upon exiting the outlet port 116 to travel through the interior of the needle and into the patient injected thereby. As may be recognized by those of ordinary skill in the pertinent art based on the teachings herein, the physical characteristics of the first valve 116 may be selected to control the fluid dynamics of each dose dispensed therethrough, such as fluid pressure and velocity, upon exiting the valve. For example, the degree of interference between the valve cover and valve seat, the axial length of the valve seam and/or the elasticity (and/or durometer) of the valve cover, each may be selected to control the fluid dynamics of each dose dispensed.

Figure 14:
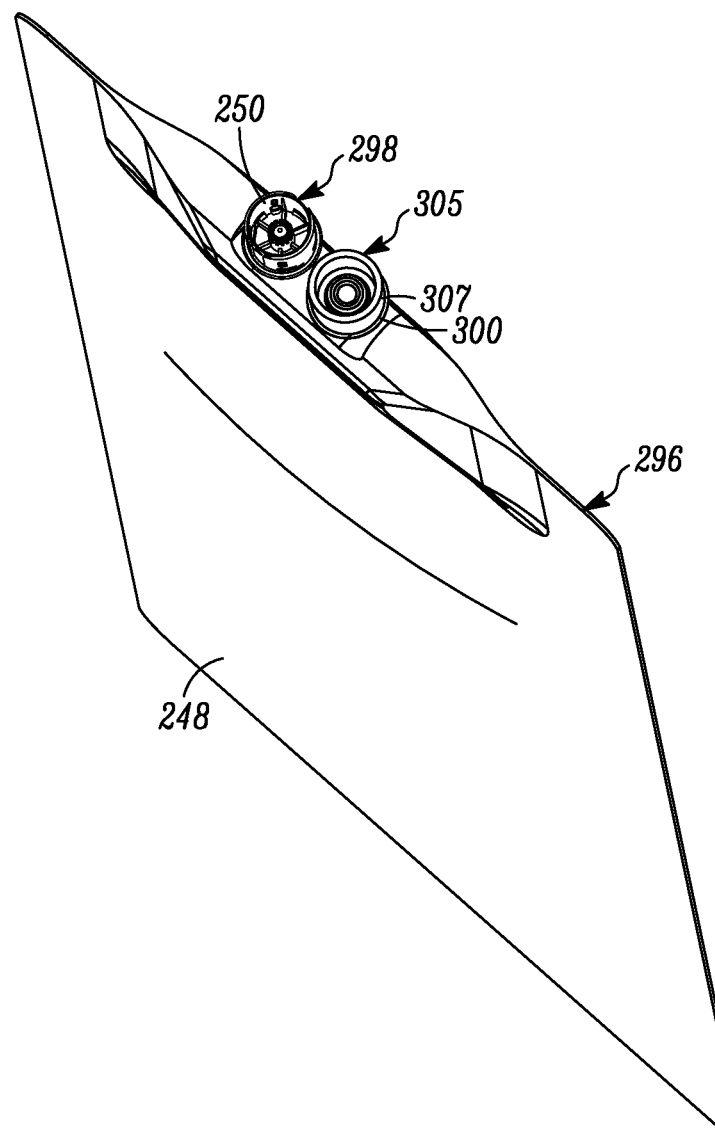
FIG. 14 is a perspective view of a multiple dose pouch connectable to the syringe or other devices of the present invention.

In FIG. 14, another pouch that is connectable to the syringes or other devices of the present invention is indicated generally by the reference numeral 296. The pouch 296 is substantially the same as the pouch 196 described above in connection with the embodiment of FIGS. 7-13, and therefore like reference numerals preceded by the number "2" instead of the numeral "1", or preceded by the numeral "3" instead of the numeral "2", are used to indicated like elements. The primary difference of the pouch 296 in comparison to the pouch 196 described above, is that the pouch 296 includes a parallel or "H" type connector. As can be seen, one leg of the "H" is defined by the filling port 298 for sterile or aseptic filling of the storage chamber 248 there-through, and the other leg of the "H" is defined by the sterile connector 305 (the male side 307 of the connector is shown) for dispensing multiple doses of the substance from the storage chamber 248 there-through and into the compression chamber of the syringe or other multiple dose device. As may be recognized by those or ordinary skill in the pertinent art based on the teachings herein, the storage chambers, pouches or other devices forming the storage chambers, and the filling ports and connectors or other inlet or outlet ports to/from the storage chambers, may take any of numerous different configurations that are currently known, or that later become known. For example, rather than being penetrable and resealable, such as by the application of laser, heat, other radiation and/or a liquid sealant thereto, the filling port may include a one-way valve connectable in fluid communication with the storage chamber. In such embodiments, rather than sterile or aseptic filling the storage chamber with a penetrable and re-sealable septum, as described above, the storage chamber may be sterile or aseptic filled through a non-piercing filling cannula or probe that is connectable in fluid communication with a one-way valve mounted on the syringe or otherwise on the device in fluid communication with the storage chamber. The filling cannula and/or valve may be constructed in the same or similar manner to that disclosed any of the following patents and patent applications, each of which is hereby expressly incorporated by reference in its entirety as part of the present disclosure: U.S. patent application Ser. No. 12/534,730, filed Aug. 3, 2009, entitled "Lyophilization Method and Device," now U.S. Pat. No. 8,272,411, which is a continuation of U.S. patent application Ser. No. 11/487,836, filed Jul. 17, 2006, entitled "Container with Valve Assembly and Apparatus and Method for Filling," now U.S. Pat. No. 7,568,509, which is a continuation of U.S. patent application Ser. No. 10/833, 371, filed Apr. 28, 2004, entitled "Container with Valve Assembly for Filling and Dispensing Substances, and Apparatus and Method for Filling," now U.S. Pat. No. 7,077,176, which, in turn, claims the benefit of similarly titled U.S. Provisional Patent Application No. 60/465,992, filed Apr. 28, 2003, and U.S. Provisional Patent Application No. 60/469,677, filed May 12, 2003, entitled "Dispenser and Apparatus and Method for Filling a Dispenser," and similarly titled U.S. Provisional Patent Application No. 60/471, 592, filed May 19, 2003; U.S. patent application Ser. No. 12/984,482, filed Jan. 4, 2011, entitled "Dispenser and Apparatus and Method for Filling a Dispenser," which is a continuation of similarly titled U.S. patent application Ser. No. 12/025,362, filed Feb. 4, 2008, now U.S. Pat. No. 7,861,750, which is a continuation of similarly titled U.S. patent application Ser. No. 11/349,873, filed Feb. 8, 2006, now U.S. Pat. No. 7,328,729, which is a continuation of similarly-titled U.S. patent application Ser. No. 10/843,902, filed May 12, 2004, now U.S. Pat. No. 6,997,219, which, in turn, claims the benefit of similarly titled U.S. Provisional Patent Application No. 60/469,677, filed May 12, 2003, and similarly titled U.S. Provisional Patent Application No. 60/471,592, filed May 19, 2003, and U.S. Provisional Patent Application No. 60/488,355, filed Jul. 17, 2003, entitled "Piston-Type Dispenser with One-Way Valve for Storing and Dispensing Metered Amounts of Substances, and Pivoting Cover for Covering Dispensing Portion Thereof," and U.S. Provisional Patent Application No. 60/539,814, filed Jan. 27, 2004, entitled "Piston-Type Dispenser with One-Way Valve for Storing and Dispensing Metered Amounts of Substances;" and U.S. patent application Ser. No. 12/724, 370, filed Mar. 15, 2010, entitled "Method for Delivering a Substance to an Eye," which is a continuation of U.S. patent application Ser. No. 10/990,164, filed Nov. 15, 2004, entitled "Delivery Device and Method of Delivery," now U.S. Pat. No. 7,678,089, which, in turn, claims the benefit of similarly titled U.S. Provisional Patent Application No. 60/519,961, filed Nov. 14, 2003.

Figure 15:
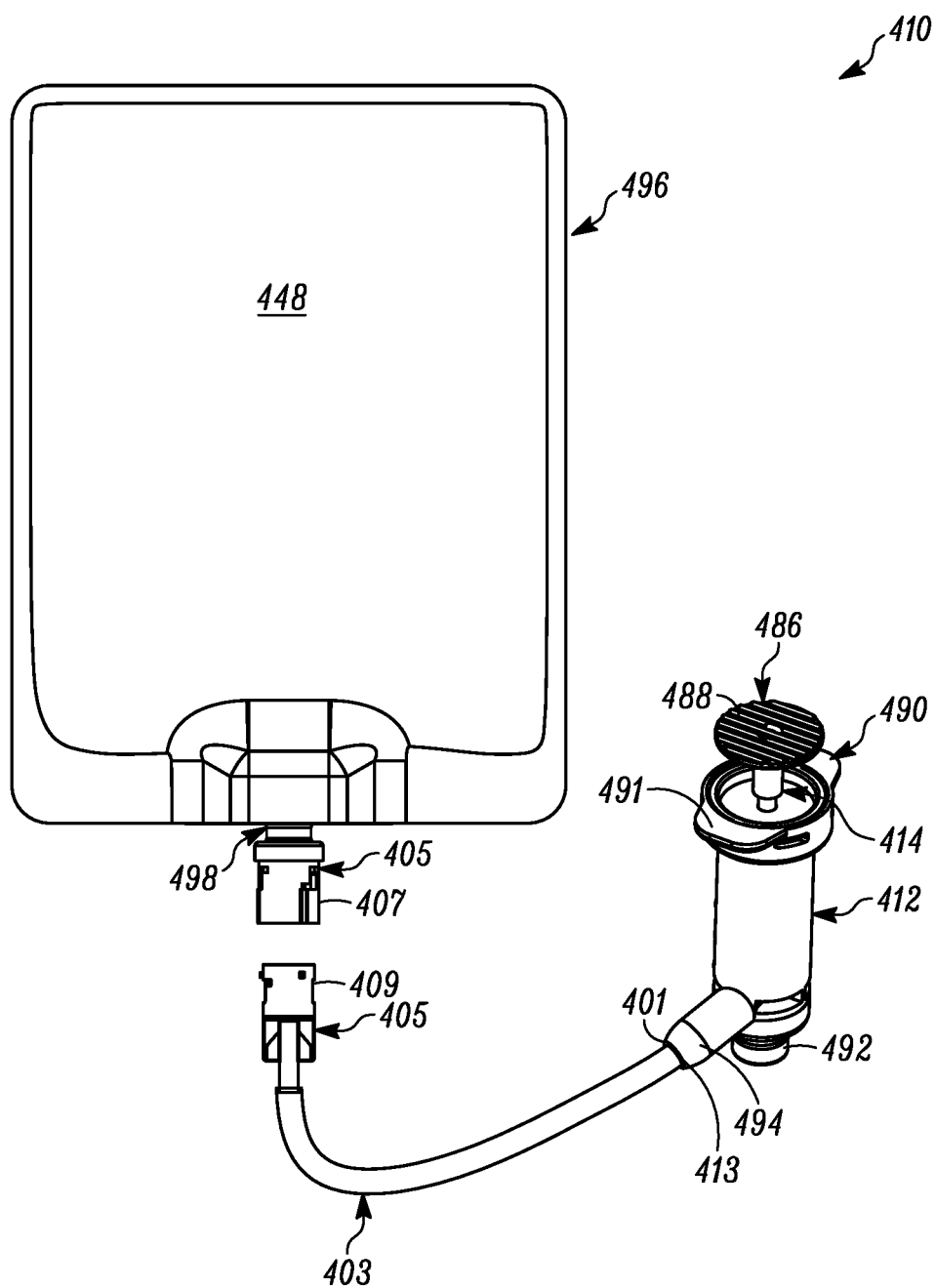
FIG. 15 is a partially schematic view, showing a perspective view of another embodiment of a multiple dose syringe, where the elastomeric plunger tip defines an integral elastic spring normally biasing the plunger in the direction from the second position toward the first position, wherein the variable-volume storage chamber is defined by an external pouch connected to the compression chamber of the syringe through flexible tubing shown in cross-section.
Figure 16:
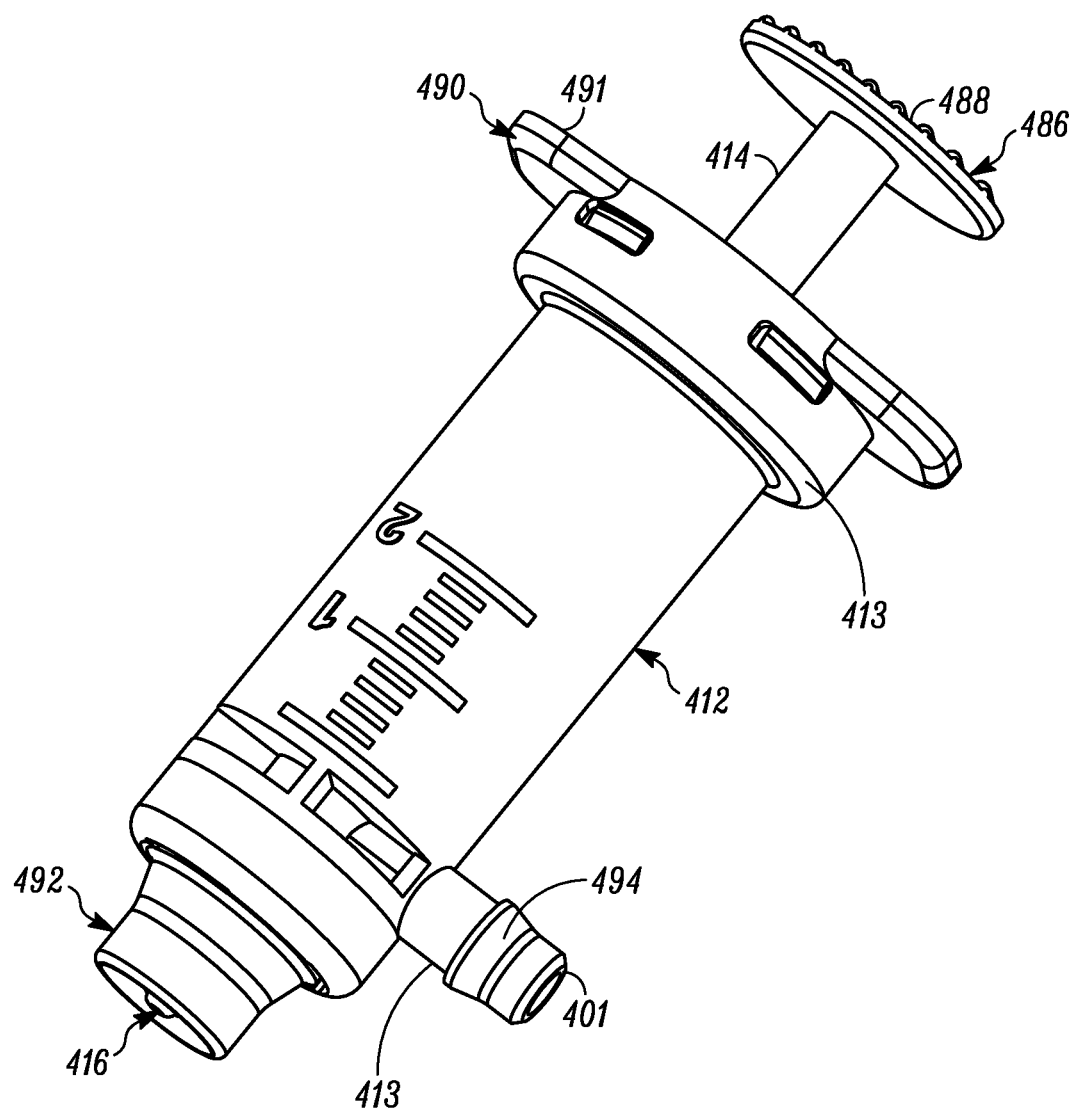
FIG. 16 is a side view of the syringe of FIG. 15.
Figure 17:
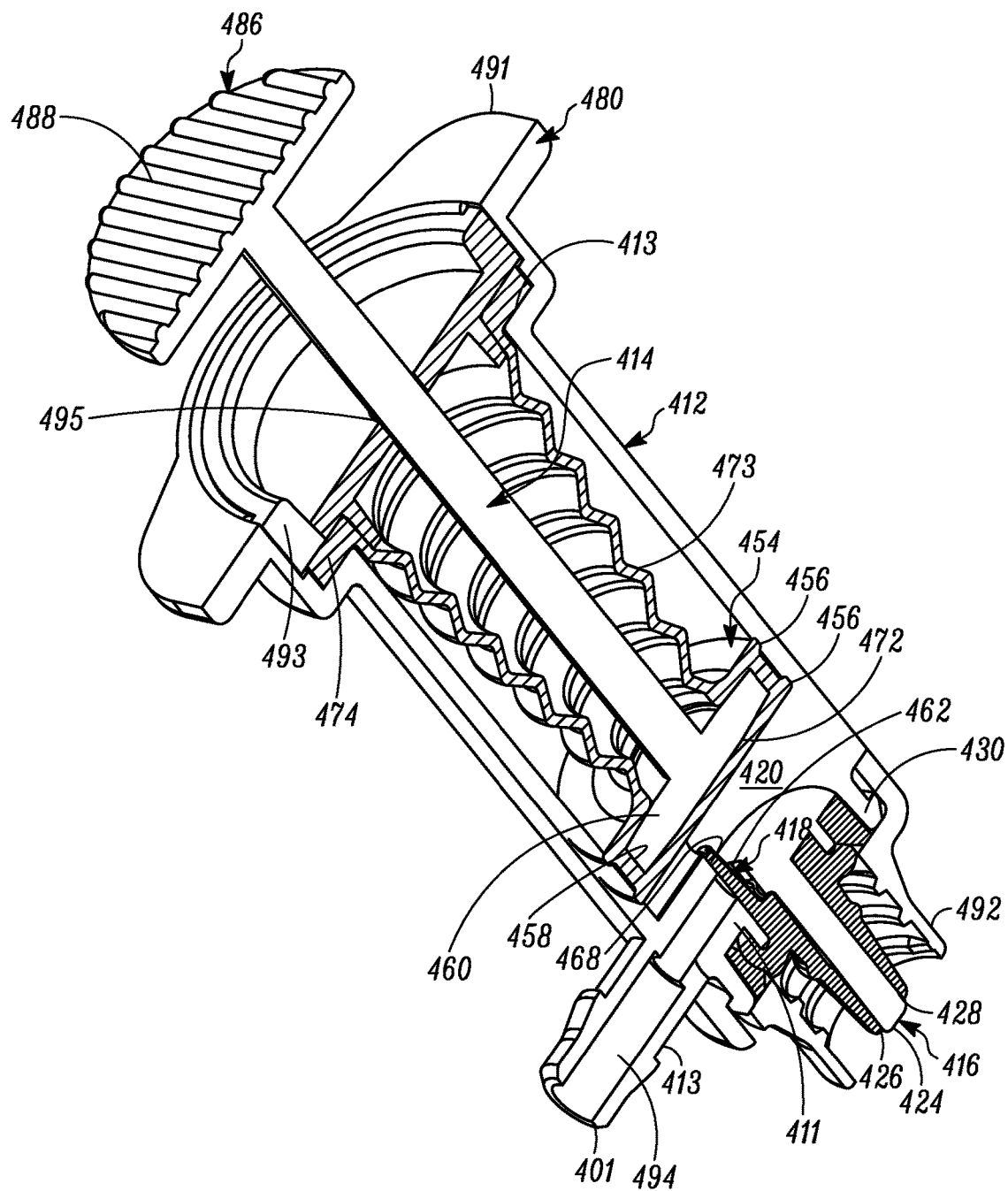
FIG. 17 is a cross-sectional perspective view of the syringe of FIG. 15.

In FIGS. 15-17, another device is indicated generally by the reference numeral 410. The device is substantially similar to the device described above in connection with FIGS. 7-13, and therefore like reference numerals preceded by the numeral "4" are used to indicate like elements. A primary difference of the device 410 in comparison to the device 110 is that the elastomeric plunger tip 454 axially extends from the proximal end of the body 412 toward the conduit 494 and includes a flexible shell 473 defining an integral spring, thereby biasing the plunger 414 from the second position toward first position. Additionally, the second valve 418 has a different configuration and is integral with the first valve member or cover 426, and the inlet conduit 494 is integral with the syringe body 412, as hereinafter described.

Similar to the embodiment described above in connection with FIGS. 7-13, the variable-volume storage chamber 448 is external to the syringe body 412 and is defined by a bladder, bag, or pouch 496. As shown in FIG. 15, the storage chamber 448 defines a universal port 498, utilized for both filling and dispensing substance. A flexible tube 403 is connected at an inlet end thereof to the port 498 of the external variable volume storage chamber 448. A sterile connector 405 may be utilized to form a sterile or aseptic connection between the universal port 498 of the variable-volume storage chamber 448 and the flexible tube 403, in accordance with the teachings of any of the patents and patent applications incorporated by reference above.

As shown best in FIG. 17, the inlet conduit 494 is integrally formed with the syringe body 412. The conduit 494 is located proximally adjacent to the base 430 of the valve member 426 and is oriented substantially perpendicular to the syringe body 412. The conduit protrudes laterally into the body 412, defining an outlet end 411 thereof, and protrudes laterally out of the body 412, defining an inlet end 413 thereof. The conduit 494 defines the inlet port 401 at the inlet end 413 thereof, which is connected to the outlet end of the flexible tube 403. The opposing outlet end of 411 the conduit 494 defines an annular end surface, which defines the relatively rigid second valve seat 468.

The first valve member or cover 426 includes the second valve 418, axially-extending from the base 430 thereof in a direction toward the plunger 414. The second valve 418 includes an elastic second valve member 462 overlying the second valve seat 468, at the outlet end of the conduit 494. The construction of the elastic second valve member 462 is such that it is normally biased into engagement with the second valve seat 468 to thereby form a normally closed second valve seam 470 therebetween. For example, the internal elastic forces generated by the second valve member 462 bias it toward the second valve seat 468. However, one of ordinary skill in the art should understand that second valve member 462 can be biased in any other suitable manner, e.g., by a spring. In the normally-closed position, as shown in FIGS. 16-17, a fluid-tight seal is formed at the valve seam 470 between the second valve member 462 and the second valve seat 468 to thereby prevent the flow of fluid through the second valve 418. However, when the pressure differential across the second valve 418, i.e., from the conduit end to the compression chamber end, exceeds a second valve opening pressure, the second valve member 462 extends away from the second valve seat 468, against the bias of elastic valve member 462, to thereby open the second valve seam 470 to, in turn, allow a dose of substance to flow from the variable-volume storage chamber, through the conduit 494, through the open second valve seam 470 and into the compression chamber 420. In the illustrated embodiment, the second valve 418 is a check or flap valve. However, as may be recognized by those of ordinary skill in the pertinent art based on the teachings herein, the second valve may be any of numerous different one-way valves described herein, or, that are currently known, or that later become known, for performing the function of the second valve as described herein, including without limitation, a duckbill valve, or an umbrella valve.

Figure 18:
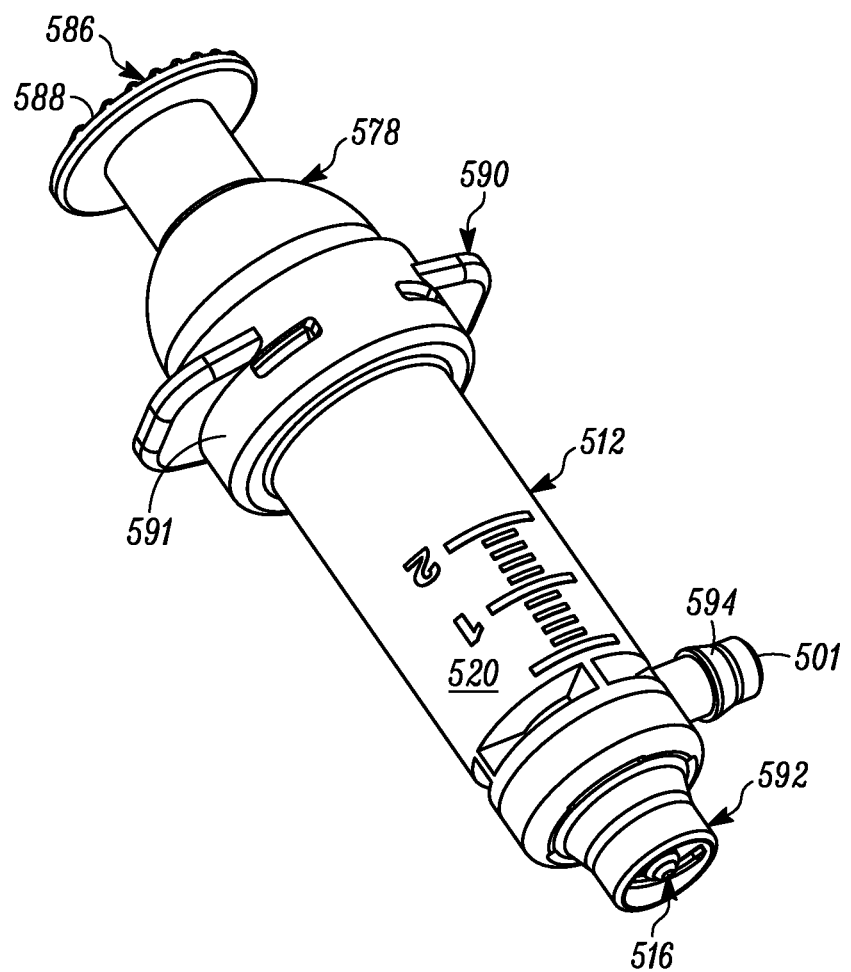
FIG. 18 is a side view of another embodiment of the multiple dose syringe, including an elastic spring assisting in biasing the plunger in the direction from the second position toward the first position, and showing the plunger in the first or unactuated position.

The plunger 414 includes an elastomeric tip 454 thereon. The distal surface of the elastomeric tip 454 defines the compression surface 472. The plunger tip 454 is sealingly engaged with the distal end of the plunger 414. The interior surface of the distal end of the plunger tip 454 defines a laterally-extending, inner annular groove 458 for receiving therein a corresponding laterally-extending, annular retaining member 460 at the distal end of the plunger 414, to fixedly secure the plunger tip thereto. In some embodiments, such as shown in FIG. 18, the plunger tip may define a pair of axially-spaced, laterally-extending, inner annular grooves 458 for receiving therein a corresponding pair of axially-spaced, laterally-extending, annular retaining members 460 of the plunger 414. However, as should be understood by those of ordinary skill in the pertinent art, the plunger tip is sealingly engageable with the distal end of the of the plunger in any of numerous different manners. The exterior surface of the distal end of the plunger tip 454 defines a pair of primary laterally-extending annular seals 456, that laterally extend annularly about the plunger tip 454 and form a sliding, fluid-tight, seal between the plunger tip 454 and the interior surface of the body 412. Other embodiments have only one seal, or more than two seals. The pair of primary laterally-extending annular seals 456 are axially spaced from one another and may be formed integral with the plunger tip 454, such as by forming thereon annular protuberances, as shown, or may be formed by sealing members, such as o-rings, or other sealing members, that are received within corresponding annular grooves or recesses formed in distal end of the plunger tip 454. As shown in FIG. 17, the pair of primary annular seals 456 form an interference fit with the substantially cylindrical interior surface of the syringe body 412 and thereby form a fluid-tight seal therebetween (and thus seal the compression chamber 420 along the plunger end).

As shown best in FIG. 17, the syringe body 412 defines, adjacent the proximal end thereof, a step increase in diameter relative to the remainder of the syringe body diameter. The step increase in diameter defines a laterally-extending annular ledge 413 distally adjacent the proximal end of the syringe body 412. The plunger tip 454 extends to the ledge 413, and defines a corresponding laterally-extending annular ring 474, at a proximal end thereof, which mounts atop and engages the annular ledge 413. As shown best in FIG. 16, the second manually-engageable surface 490 includes a rear cover 491 mounted thereon, and extending across the proximal opening of the syringe body 412. The rear cover 491 defines an axially-extending annular protuberance 493, extending from the cover 491 and into the proximal end of the syringe body 412 in fitting engagement with the substantially cylindrical interior surface of the syringe body 412. The distal end of the annular protuberance 493 fixedly secures the ring 474 in place atop the ledge 413, creating a fluid-tight seal therebetween. Thus, the ring 474 functions as a secondary or environmental seal that prevents contaminants from entering into the syringe body 412 from the proximal end thereof. In the illustrated embodiment, the rear cover 491 is over-molded or otherwise co-molded to the syringe body 412 and the second manually engageable surface 490, as shown. The rear cover 491 further defines an approximately central aperture 495, through which slidingly extends the plunger 414.

The plunger tip 454 defines a flexible shell 473 between the proximal and distal ends thereof, surrounding a portion of the plunger 414 therein. In the illustrated embodiment, the flexible shell 473 forms an elastic bellows, defining an integral spring. In some embodiments, the bellows may be made of a silicone material. In other embodiments the bellows may be made of other flexible materials, currently known or that later become known, capable of performed the function of the bellows as described herein. The integral spring of the bellows 473 normally biases the plunger 414 from second, actuated position toward the first, unactuated position. However, as may be recognized by those of ordinary skill in the pertinent art based on the teachings herein, the flexible shell may take any of numerous different configurations that are currently known, or that later become known, for performing the function of the shell as described herein.

As best shown in FIG. 17, the compression chamber 420 is formed between the compression surface 472 and the first valve 416. When the plunger 414 is displaced from the first position toward the second position, the bellows 473 is axially extended, and the compression surface 472 pressurizes the substance within the compression chamber 420 to a pressure exceeding the valve opening pressure of the first valve 416. Substance is thereby dispensed out of the syringe 410 in the same manner as described above in connection with the embodiment of FIGS. 1-6B. When the plunger 414 is released, the integral elastic spring of the bellows naturally rebounds and retracts the plunger 414 from the second position back toward the first position, thereby creating a partial vacuum in the compression chamber 420, in the same manner as described above in connection with the embodiments of FIGS. 1-6B. The partial vacuum created in the compression chamber 420 creates a pressure differential across the second valve 418 exceeding the valve opening pressure. The resulting suction force causes another dosage of the substance in the variable volume storage chamber 448 to flow through the conduit 494 and the second valve seam 470 of the second valve 418 and, in turn, into the compression chamber 420.

Figure 19:
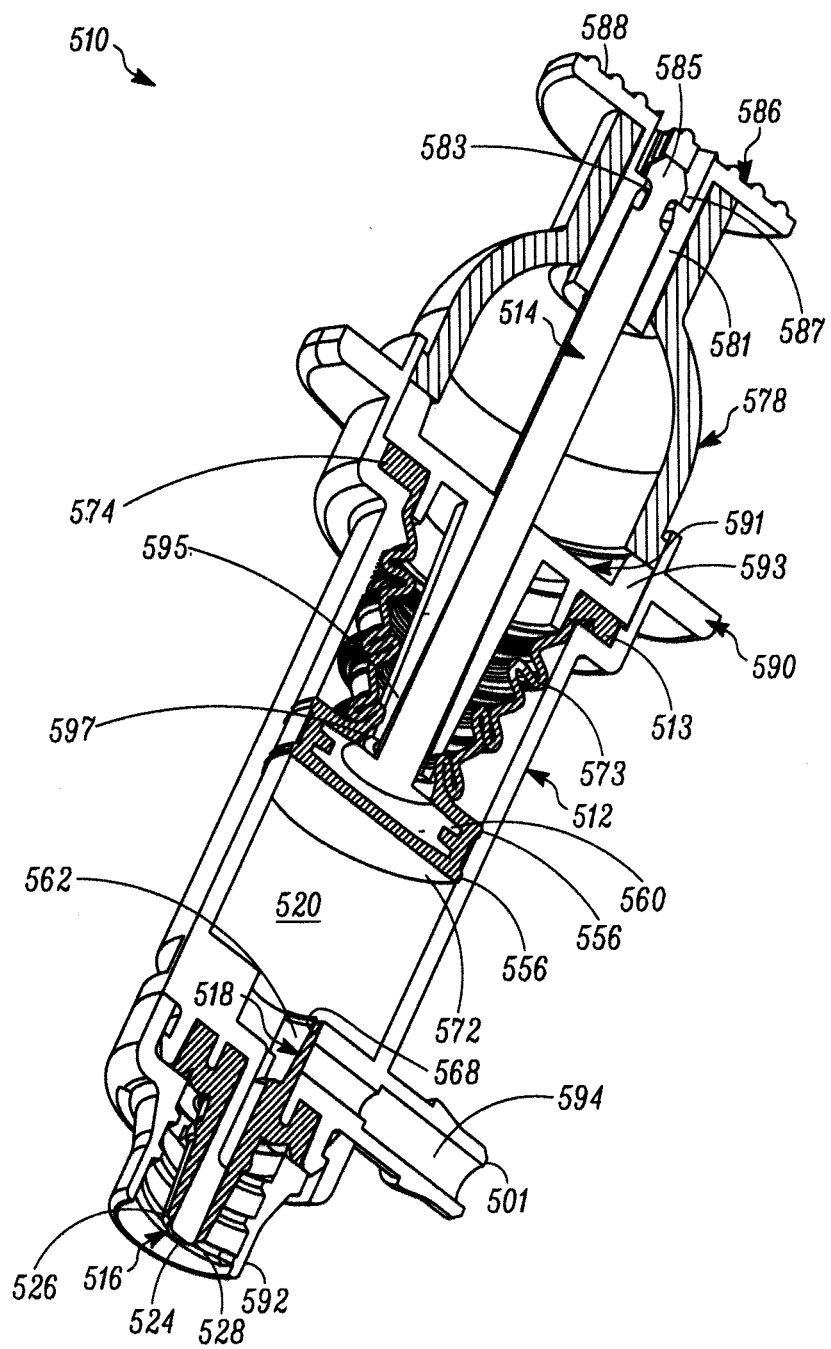
FIG. 19 is a cross-sectional perspective view of the syringe of FIG. 18.

In FIGS. 18-19, another device is indicated generally by the reference numeral 510. The device is substantially similar to the device described above in connection with FIGS. 15-17, and therefore like reference numerals preceded by the numeral "5" are used to indicate like elements. A primary difference of the device 510 in comparison to the device 410 is that the syringe 510 further includes a spring 578, providing a return force of the plunger from the second position toward the first position, as hereinafter described.

As shown in FIG. 19, the rear cover 591 is fittingly inserted into the proximal end of the syringe body 512 to secure the ring 574 in place against the ledge 513. The rear cover 591 defines an approximately central axially-elongated hollow projection 595 extending distally within the body 512, slidably receiving a portion of the plunger 514 therein, and defining an annular distal end surface 597 configured to engage the distal end of the plunger 514 and prevent further proximal movement thereof, e.g., substantially past the first position.

The spring 578 is coupled between the cap 586 and the rear cover 591, and extends annularly about a portion of the plunger 514. Unlike the embodiment of FIGS. 15-17, where the cap 486 is integral with the proximal end of the plunger 414, the cap 586 includes an approximately central axially-elongated hollow cylindrical projection 581 for fixedly securing the cap 586 to a proximal portion of the plunger 514. The projection 581 defines an annular and inwardly tapered protuberance 583 distally spaced from the underside of the surface 588, to define a space 587 therebetween. The plunger 514 defines a corresponding proximal tip portion 585 configured to slide over the protuberance 583 (or vice versa). When the plunger 514 is slid into the projection 581 and snap into the space between the projection 581 (or the cap 586 slid over the tip portion 585), the parts snap together with the tip 585 secured in the space 587. This facilitates assembly of the device, so that the spring 578 can be slid over the plunger and then the cap 586 connected to the plunger 514. As should be understood by those of ordinary skill in the pertinent art however, the cap 586 and the plunger 514 may be fixedly secured to one another in any of numerous different manners. In yet other embodiment, the cap 586 and the plunger 514 are integral, similar to the plunger 414 and the cap 486 in FIGS. 15-17.

The force of the spring 578 secures the distal end of the spring 578 to the rear cover 591, and the proximal end of the spring 570 to the cap 586. When the plunger 514 is depressed, the spring 578 is compressed between the cap 586 and the rear cover 591, thereby storing energy therein. When the force on the plunger 514 is released, the stored spring force naturally biases the plunger from the second position toward the first position, as does the bellows 573. Thus, the spring 578 functions similarly to the bellows 573 and provides additional returning force, biasing the plunger 514 from the second position toward the first position. In other embodiments, the flexible bellows 573 does not define an integral spring, and all the spring force is supplied by the spring 578. In the illustrated embodiments of FIGS. 18 and 19, the spring 578 is an approximately dome-shaped elastomeric spring. However, as should by recognized by those of ordinary skill in the pertinent art, the spring 578 may take the form of any spring capable of performing the function of the spring 578 as described herein.

Figure 20:
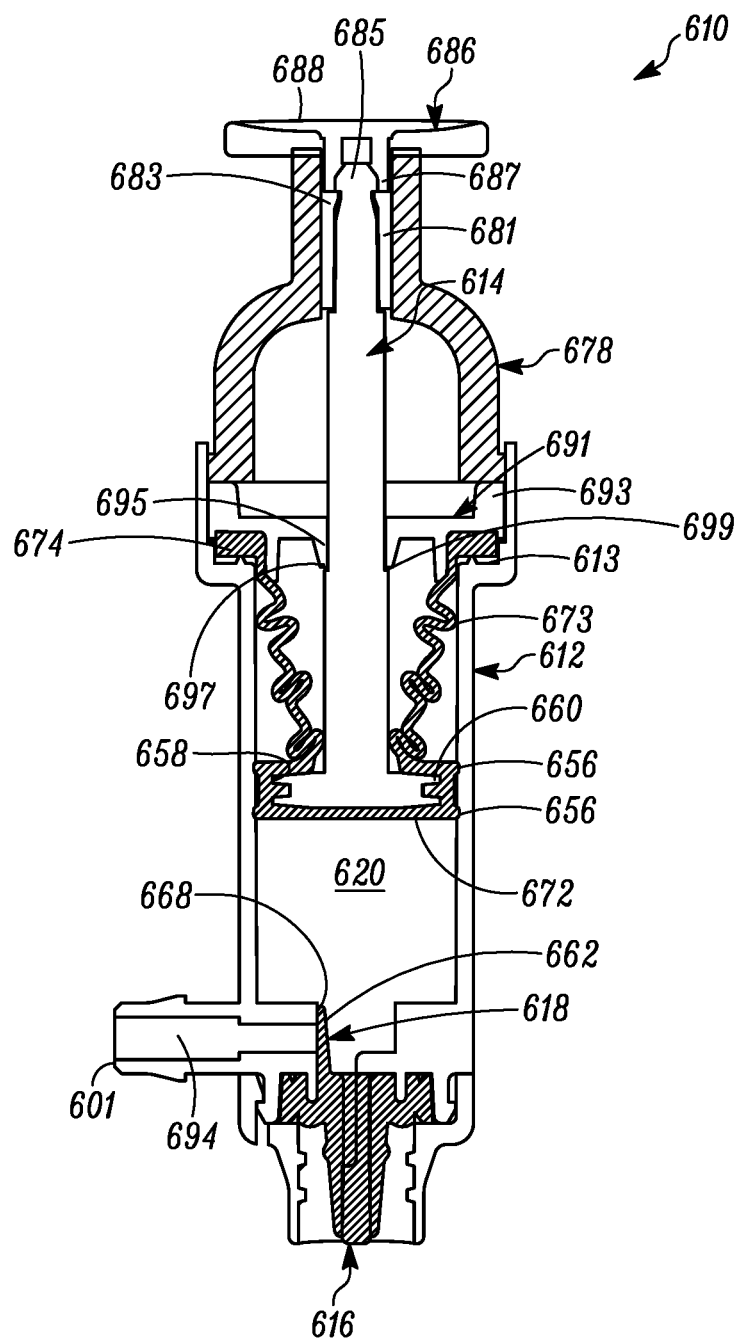
FIG. 20 is a cross-sectional side view of another embodiment of the multiple dose syringe, where the plunger defines a step increase in diameter between a proximal portion thereof and a distal portion thereof.
Figure 21:
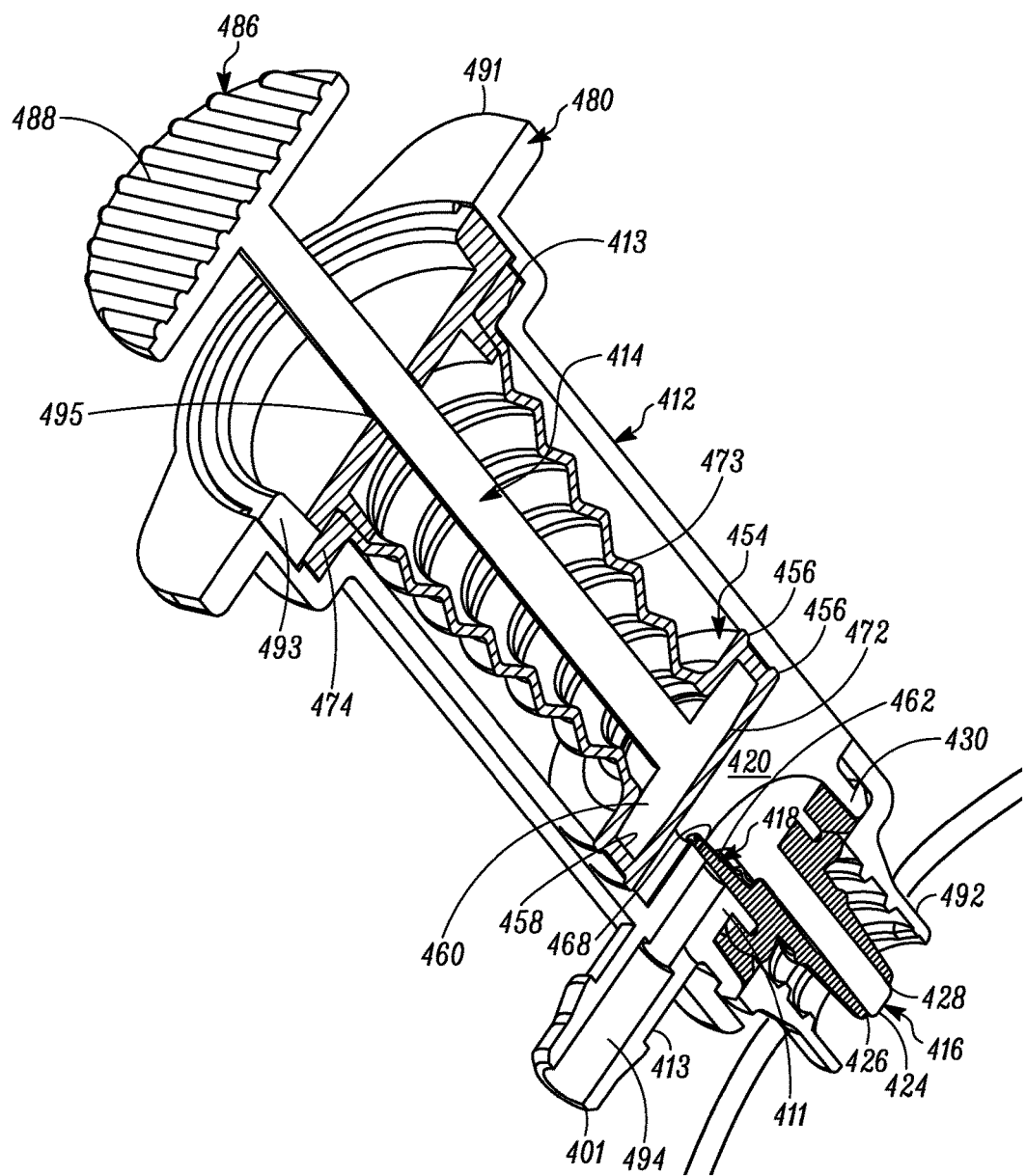
FIG. 21 is the syringe of FIG. 17, with a disposable shield attached thereto.

In FIG. 20, another device is indicated generally by the reference numeral 610. The device is substantially similar to the device described above in connection with FIGS. 18-19, and therefore like reference numerals preceded by the numeral "6" are used to indicate like elements. A primary difference of the device 610 in comparison to the device 510 is that the plunger 614 defines a step increase in diameter at approximately a middle point thereof, thereby creating an annular ledge 699 at the interface between the different diameter portions. The rear cover 691 defines a relatively shorter projection 695, the distal end surface 697 thereof being engageable with the annular ledge 699 to prevent further proximal movement of the plunger 614, e.g., substantially past the first position.

As may be recognized by those of ordinary skill in the pertinent art based on the teachings herein, numerous changes and modifications may be made to the above-described and other embodiments of the present invention without departing from its scope as defined in the claims. For example, any of the external variable-volume storage chambers herein can be utilized with any of the syringes of FIG. 7 et. seq. As another example, the components of the syringe may be made of any of numerous different materials that are currently known, or that later become known for performing the function(s) of each such component. Similarly, the components of the syringe may take any of numerous different shapes and/or configurations. Also, the syringe may be used to dispense any of numerous different types of fluids or other substances for any of numerous different applications, including, for example, medicaments, pharmaceuticals, vaccines, liquid nutrition products, supplements, and numerous other products that are currently known, or later become known. In addition, the storage chamber need not be a variable-volume storage chamber. For example, in another embodiment, the storage chamber defines a substantially fixed volume, but includes a sterile filter, such as a micro-filter of a type known to those of ordinary skill in the pertinent art, that is coupled in fluid communication between the storage chamber and ambient atmosphere to allow air to flow into the storage chamber, but that sterilizes any such air that flows therethrough in order to maintain the interior of the variable-volume storage chamber sterile. In addition, the characteristics of the syringe may be adjusted, including for example the shape and/or configuration of the body and/or plunger, the shape/ and or configurations of the variable-volume storage chamber, the volume of the metered dosages, and/or the valve opening pressure(s), to meet the requirements of any of numerous different applications and/or products to be dispensed. Accordingly, this detailed description of embodiments is to be taken in an illustrative, as opposed to a limiting sense.

What is claimed is:

1. A method comprising:
   i. storing multiple doses of a substance to be dispensed in a device comprising:
      a storage chamber that is hermetically sealed from ambient atmosphere and configured to contain multiple doses of the substance therein;
      a device body hermetically sealed from ambient atmosphere; and
      a sterile connector configured to form a sterile flow connection between the storage chamber and the device body, the sterile connector configurable between a disconnected position and a connected position, wherein in the connected position the sterile connector places the storage chamber and the device body in fluid communication with each other and defines a sterile flow path between the storage chamber and the device body that is hermetically sealed from ambient atmosphere, and in the disconnected position the sterile connector prevents fluid communication between the storage chamber and the device body, maintains an interior of the storage chamber and an interior of the device body hermetically sealed from ambient atmosphere, and seals with respect to ambient atmosphere all surfaces of the sterile connector over which fluid flows in the connected position, thereby allowing aseptic transfer of fluid between the storage chamber and the device body;
      wherein the device body includes:
      a first valve defining an outlet thereof and a first valve opening pressure;
      a second valve defining a second valve opening pressure, and connectible in fluid communication with substance flow from the storage chamber;
      a compression surface movable between first and second positions;
      a compression chamber defined between the compression surface and the first valve; and
      a connector located at a distal end of the device adjacent to the outlet of the first valve and adapted to receive thereon an administering member for administering a dispensed dose of substance to a patient such that one or more of (i) the outlet of the first valve is in fluid communication with the connector without any structure therebetween; (ii) the outlet of the first valve is in fluid communication with an administering member connected to the connector without any structure therebetween; (iii) substance flowing out of the outlet of the first valve flows into the administering member without contacting the connector; or (iv) no portion of the device body is located downstream of the outlet of the first valve in a flow path of the substance between the outlet of the first valve and the administering member;
      wherein (i) movement of the compression surface in the direction from the first position toward the second position creates a pressure differential across the first valve exceeding the first valve opening pressure and dispenses a dose of substance in the compression chamber through the outlet of the first valve and out of the device, and (ii) movement of the compression surface in a direction from the second position toward the first position creates a pressure differential across the second valve exceeding the second valve opening pressure and, when the sterile connector is in the connected position, causes another dose of substance to flow from the storage chamber through the second valve and into the compression chamber;
   ii. aseptically transferring a dose of substance from the storage chamber into the compression chamber,
   iii. compressing the dose of substance in the compression chamber above the first valve opening pressure by moving the compression surface in the direction from the first position toward the second position;
   iv. releasing the dose of substance through the first valve;
   v. transferring the dose of substance into the administering member releasably attached to the device for administering a dispensed dose of substance to a patient, without said dose passing through or contacting any structure between the outlet of the first valve and the administering member;
   vi. throughout steps i through iv, maintaining the substance in the storage chamber and compression chamber in one or more of a sterile or an aseptic condition and preventing said dose from exposure to ambient atmosphere; and
   vii. repeating steps ii, iii, iv, and vi with the same device.

2. A method as defined in claim 1, wherein the compressing step includes manually actuating an actuator to compress the dose of substance in the compression chamber above the first valve opening pressure.

3. A method as defined in claim 2, further comprising moving the compression surface in a direction from the second position toward the first position and, in turn, creating at least a partial vacuum in the compression chamber and exceeding the second valve opening pressure and causing said another dose of substance to flow from the storage chamber into the compression chamber.

4. A method as defined in claim 3, wherein the moving step includes biasing the compression surface in a direction toward the first position and releasing the actuator.

5. A method as defined in claim 1, wherein the second valve comprises an inlet valve of the device body.

6. A method as defined in claim 1, further including either parenterally or enterally administering the released dose of substance to the patient.

7. A method as defined in claim 6, wherein (i) the parenterally administering member includes a needle coupled in fluid communication with the first valve and the parenterally administering step includes injecting the dose of substance through the needle, or (ii) the enterally administering step includes orally or nasally administering the dose of substance to the patient.

8. A method as defined in claim 7, further comprising connecting a disposable shield adjacent to the outlet of the first valve to facilitate oral or nasal administration of the dose of substance to the patient.

9. A method as defined in claim 8, further comprising replacing the disposable shield when the administering step is repeated.

10. A method as defined in claim 6, further comprising parenterally or enterally administering a second released dose of substance to a second patient.

11. A method as defined in claim 7, further comprising parenterally or enterally administering a second released dose of substance to a second patient, wherein (i) the administering member includes a needle coupled in fluid communication with the first valve and the administering step includes injecting the second dose of substance through a second needle coupled in fluid communication with the first valve, or (ii) the administering step includes orally or nasally administering the second dose of substance to the patient.

12. A method as defined in claim 1, wherein the first valve includes a rigid valve seat and an elastic valve member that forms a normally closed, axially elongated valve seam and one or more of (i) the elastic valve member defines a progressively decreasing wall thickness in a direction from an inlet toward an outlet of the valve seam, or (ii) the valve seat defines a progressively increasing width or diameter in a direction from the inlet toward the outlet of the valve seam, and the method further comprises substantially preventing the passage of substance through the valve seam when a pressure differential across the first valve is less than the first valve opening pressure, and allowing the passage of substance through the seam when a pressure differential across the first valve exceeds the first valve opening pressure.

13. A method as defined in claim 1, further comprising, before step vii, detaching said administering member from the device and releasably attaching another administering member.

14. A method as defined in claim 1, further comprising, prior to step ii, forming a sterile connection between the storage chamber and the device body to allow aseptic transfer of substance between the storage chamber and the device body.

15. A method as defined in claim 14, wherein the forming step includes configuring the sterile connector from the disconnected position to the connected position.

16. A method as defined in claim 15, further comprising disconnecting the storage chamber from the device body and connecting a second storage chamber to the device body without exposing any substance flow path in the second storage chamber and in the device body to ambient atmosphere.

17. A method as defined in claim 1, wherein the aseptically transferring step includes creating at least a partial vacuum in the compression chamber and, in turn, causing the dose of substance to flow from the storage chamber into the compression chamber.

18. A method as defined in claim 1, wherein the storage chamber is a variable-volume storage chamber, and the aseptically transferring step reduces the volume of the variable-volume storage chamber in an amount substantially equal to the volume of the dose.

19. A method as defined in claim 1, wherein the first valve includes a valve seat and a valve member that forms a normally closed valve seam, wherein the valve seam defines said outlet of the first valve.

20. A multiple dose device, comprising:
a storage chamber hermetically sealed from ambient atmosphere and configured to contain multiple doses of a substance therein;
a device body hermetically sealed from ambient atmosphere; and
a sterile connector configured to form a sterile flow connection between the storage chamber and the device body, the sterile connector configurable between a disconnected position and a connected position, wherein in the connected position the sterile connector places the storage chamber and the device body in fluid communication with each other and defines a sterile flow path between the storage chamber and the device body that is hermetically sealed from ambient atmosphere, and in the disconnected position the sterile connector prevents fluid communication between the storage chamber and the device body, maintains an interior of the storage chamber and an interior of the device body hermetically sealed from ambient atmosphere, and seals with respect to ambient atmosphere all surfaces of the sterile connector over which fluid flows in the connected position, thereby allowing aseptic transfer of fluid between the storage chamber and the device body;
wherein the device body includes
a first valve defining an outlet thereof and a first valve opening pressure;
a second valve defining a second valve opening pressure, and connectible in fluid communication with substance flow from the storage chamber;
a compression surface movable between first and second positions, and
a compression chamber defined between the compression surface and the first valve; and
a connector located at a distal end of the device adjacent to the outlet of the first valve and adapted to receive thereon an administering member for administering a dispensed dose of substance to a patient such that one or more of (i) the outlet of the first valve is in fluid communication with the connector without any structure therebetween; (ii) the outlet of the first valve is in fluid communication with an administering member connected to the connector without any structure therebetween; (iii) substance flowing out of the outlet of the first valve flows into the administering member without contacting the connector; or (iv) no portion of the device body is located downstream of the outlet of the first valve in a flow path of the substance between the outlet of the first valve and the administering member;
wherein (i) movement of the compression surface in a direction from the first position toward the second position creates a pressure differential across the first valve exceeding the first valve opening pressure and dispenses a dose of substance in the compression chamber through the outlet of the first valve and out of the device, and (ii) movement of the compression surface in a direction from the second position toward the first position creates a pressure differential across the second valve exceeding the second valve opening pressure and, when the sterile connector is in the connected position, causes another dose of substance to flow from the storage chamber through the second valve and into the compression chamber.

21. A multiple dose device as defined in claim 20, further comprising a manually engageable actuator coupled to the compression surface for moving the compression surface between the first and second positions;
and wherein movement of the compression surface in a direction from the second position to the first position creates at least a partial vacuum in the compression chamber that, when the sterile connector is in the connected position, causes said another dose of substance to flow from the storage chamber through the second valve and into the compression chamber.

22. A multiple dose device as defined in claim 20, wherein the storage chamber is a variable-volume storage chamber.

23. A multiple dose device as defined in claim 20, wherein the first valve includes an elastic valve member defining a normally closed, axially-elongated seam with an inlet and an outlet, and wherein the elastic valve member is configured to maintain the compression chamber and any substance therein sealed from the ambient atmosphere throughout dispensing of substance through the outlet of the valve seam.

24. A multiple dose device as defined in claim 20, wherein one of more of (i) the first valve or (ii) one of more of the second valve or the storage chamber moves toward the other when the compression surface is moved from the first position toward the second position, and moves away from the other when the compression surface is moved from the second position toward the first position.

25. A multiple dose device as defined in claim 20, wherein the first valve is located at a distal end of the device body, and the storage chamber is one of (i) located external to the device body or (ii) located internal to the device body.

26. A multiple dose device as defined in claim 20, further comprising a plunger slidably received within the device body, wherein the first valve is located adjacent to a distal end of the device body, the second valve is located adjacent to a distal end of the plunger, and the compression surface is located adjacent to a distal end of the plunger.

27. A multiple dose device as defined in claim 20, wherein the storage chamber is located external to the device, and the sterile connector is configured between an outlet of the storage chamber and an inlet of the second valve and to form a sterile flow connection between the storage chamber and the inlet of the second valve.

28. A multiple dose device as defined in claim 20, wherein the connector is adapted to have connected thereto and receive thereon an administering member that is one or more of (i) a needle for injecting a dose of substance into a patient, or (ii) a shield to facilitate one or more of oral or nasal dosing of the substance to be dispensed.

29. A multiple dose device as defined in claim 28, further comprising one or more of (i) a needle that is connectable to the connector for injecting a dose of substance into a patient, or (ii) a shield that is connectable to the connector to facilitate one or more of oral or nasal dosing of the substance to be dispensed.

30. A multiple dose device as defined in claim 29, further comprising one or more of (i) a plurality of needles, wherein each needle is connectable to the connector for injecting a dose of substance into a respective patient and is disconnectable from the connector to allow the connection of a different needle to the connector for injecting a dose of substance into another patient, or (ii) a plurality of shields, wherein each shield is connectable to the connector to facilitate one or more of oral or nasal dosing of the substance to a respective patient and is disconnectable from the connector to allow connection of a different shield to the connector to facilitate one or more of oral or nasal dosing of the substance to another patient.

31. A multiple dose device as defined in claim 20, wherein the second valve comprises one or more of a check valve, a duckbill valve, a flapper valve or an umbrella valve.

32. A multiple dose device as defined in claim 20, wherein the first valve includes a valve seat and a valve member that forms a normally closed valve seam, wherein the valve seam defines said outlet of the first valve.

* * * * *